(12) United States Patent
Drohan et al.

(10) Patent No.: US 6,783,968 B2
(45) Date of Patent: Aug. 31, 2004

(54) METHODS FOR STERILIZING PREPARATIONS OF GLYCOSIDASES

(75) Inventors: William N. Drohan, Springfield, VA (US); Wilson Burgess, Clifton, VA (US); David M. Mann, Gaithersburg, MD (US); Martin J. MacPhee, Montgomery Village, MD (US)

(73) Assignee: Clearant, Inc., Los Angeles, CA (US)

( * ) Notice: Subject to any disclaimer, the term of this patent is extended or adjusted under 35 U.S.C. 154(b) by 0 days.

(21) Appl. No.: 09/960,704

(22) Filed: Sep. 24, 2001

(65) Prior Publication Data

US 2003/0059920 A1 Mar. 27, 2003

(51) Int. Cl.[7] .......................... A01N 63/00; C12N 9/24; C12N 9/00; C12N 13/00
(52) U.S. Cl. ................. 435/200; 435/173.1; 435/173.2; 435/183; 424/94.3
(58) Field of Search .............................. 435/200, 173.1, 435/173.2, 183; 422/22; 424/94.1, 94.3

(56) References Cited

U.S. PATENT DOCUMENTS

| | | |
|---|---|---|
| RE23,195 E | 2/1950 | Arno Brasch |
| 2,832,689 A | 4/1958 | Proctor et al. |
| 2,920,969 A | 1/1960 | Stoddard |
| 2,962,380 A | 11/1960 | Wertheim |
| 3,620,944 A | 11/1971 | Tanito |
| 3,743,480 A | 7/1973 | Falk |
| 3,779,706 A | 12/1973 | Nablo |
| 3,962,038 A | 6/1976 | Kawashima et al. .......... 195/68 |
| 4,136,094 A | 1/1979 | Condie |
| 4,251,437 A | 2/1981 | Rasmussen et al. |
| 4,282,863 A | 8/1981 | Beigler et al. |
| 4,330,626 A | 5/1982 | Blair et al. |
| 4,336,247 A | 6/1982 | Eriksen |
| 4,370,264 A | 1/1983 | Kotitschke et al. |

(List continued on next page.)

FOREIGN PATENT DOCUMENTS

| | | |
|---|---|---|
| CA | 2056619 | 10/1991 |
| EP | 0 310 316 | 4/1989 |
| EP | 0 334 679 | 9/1989 |
| EP | 0808167 B1 | 6/2002 |
| EP | 0820301 B1 | 7/2002 |
| JP | 408098688 A | 4/1996 |
| WO | WO 90/00907 | 2/1990 |
| WO | WO 91/16060 | 10/1991 |
| WO | WO 95/03071 | 2/1995 |
| WO | WO 00/28552 | 5/2000 |
| WO | WO 00/52031 | 9/2000 |

OTHER PUBLICATIONS

P.V. Kapanin et al., "Feasibility of liposome cryoradiation sterilization," Khimiko–Farmatsevticheskii Zhurnal, 1988, vol. 22(4), Abstract, pp. 479–482.

(List continued on next page.)

Primary Examiner—Christopher R. Tate
Assistant Examiner—Randall Winston
(74) Attorney, Agent, or Firm—Fleshner & Kim, LLP

(57) ABSTRACT

Methods are disclosed for sterilizing preparations of glycosidases to reduce the level therein of one or more active biological contaminants or pathogens, such as viruses, bacteria (including inter- and intracellular bacteria, such as mycoplasmas, ureaplasmas, nanobacteria, chlamydia, rickettsias), yeasts, molds, fungi, single or multicellular parasites, prions or similar agents responsible, alone or in combination, for TSEs. These methods involve sterilizing preparations of glycosidases, such as alpha-glucosidase or alpha-galactosidase, with irradiation.

56 Claims, 6 Drawing Sheets

Gamma Irradiation of a Galactosidase in the Absence or Presence of Ascorbate Alone or in Combination with Gly-Gly

U.S. PATENT DOCUMENTS

| | | | |
|---|---|---|---|
| 4,409,105 A | 10/1983 | Hayashi et al. | |
| 4,472,840 A | 9/1984 | Jefferies | |
| 4,620,908 A | 11/1986 | Van Duzer | |
| 4,727,027 A | 2/1988 | Wiesehahn et al. | 435/173 |
| 4,877,866 A | 10/1989 | Rudnick et al. | 530/387 |
| 4,894,253 A | 1/1990 | Heineman et al. | 427/36 |
| 4,931,361 A | 6/1990 | Baldeschwieler et al. | |
| 4,933,145 A | 6/1990 | Uchida et al. | |
| 4,946,648 A | 8/1990 | Dichtelmüller et al. | |
| 4,963,356 A | 10/1990 | Calenoff et al. | |
| 4,994,237 A | 2/1991 | Login et al. | 422/21 |
| 5,000,951 A | 3/1991 | Bass et al. | |
| 5,002,766 A | 3/1991 | Ransberger et al. | 424/94.2 |
| 5,012,503 A | 4/1991 | Nambu et al. | |
| 5,044,091 A | 9/1991 | Ueda et al. | |
| 5,106,619 A | 4/1992 | Wiesehahn et al. | |
| 5,134,295 A | 7/1992 | Wälischmiller | |
| 5,185,371 A | 2/1993 | Rubinstein | |
| 5,226,065 A | 7/1993 | Held et al. | |
| 5,362,442 A | 11/1994 | Kent | |
| 5,418,130 A | 5/1995 | Platz et al. | |
| 5,460,962 A | 10/1995 | Kemp | |
| 5,510,122 A | 4/1996 | Sreebny et al. | |
| 5,585,247 A * | 12/1996 | Habenstein | |
| 5,603,894 A | 2/1997 | Aikus et al. | |
| 5,609,864 A | 3/1997 | Shanbrom | |
| 5,637,451 A | 6/1997 | Ben-Hur et al. | |
| 5,712,086 A | 1/1998 | Horowitz et al. | |
| 5,730,933 A | 3/1998 | Peterson | |
| 5,817,528 A | 10/1998 | Böhm et al. | |
| 5,837,313 A | 11/1998 | Ding et al. | |
| 5,856,172 A | 1/1999 | Greenwood et al. | |
| 5,881,534 A | 3/1999 | Ahlqvist et al. | |
| 5,911,951 A | 6/1999 | Girardot et al. | 422/28 |
| 5,958,669 A | 9/1999 | Ogle et al. | 435/1.1 |
| 5,965,349 A | 10/1999 | Lin et al. | 435/2 |
| 5,981,163 A | 11/1999 | Horowitz et al. | |
| 5,986,168 A | 11/1999 | Noishiki | |
| 6,010,719 A | 1/2000 | Remon et al. | |
| 6,046,024 A | 4/2000 | Burton et al. | |
| 6,049,025 A | 4/2000 | Stone et al. | |
| 6,060,233 A | 5/2000 | Wiggins | |
| 6,066,626 A | 5/2000 | Yew et al. | |
| 6,087,141 A | 7/2000 | Margolis-Nunno et al. | |
| 6,120,592 A | 9/2000 | Brault et al. | |
| 6,159,490 A | 12/2000 | Deghenghi | |
| 6,171,549 B1 * | 1/2001 | Kent | |
| 6,187,572 B1 | 2/2001 | Platz et al. | |
| 6,190,855 B1 | 2/2001 | Herman et al. | |
| 6,197,207 B1 | 3/2001 | Chapman et al. | |
| 6,214,534 B1 | 4/2001 | Horowitz et al. | |
| 6,235,508 B1 | 5/2001 | Sowemimo-Coker et al. | |
| 6,258,821 B1 | 7/2001 | Stogniew et al. | |
| 6,312,931 B1 | 11/2001 | O'Dwyer et al. | 435/173.1 |
| 6,346,216 B1 | 2/2002 | Kent | 422/22 |
| 6,358,284 B1 | 3/2002 | Fearnot et al. | 623/23.72 |
| 6,375,989 B1 | 4/2002 | Badylak et al. | 424/551 |
| 6,383,732 B1 | 5/2002 | Stone | 435/1.1 |
| 6,383,810 B2 | 5/2002 | Fike et al. | 435/384 |
| 6,384,419 B1 | 5/2002 | Purtle | 250/526 |
| 6,461,630 B1 | 10/2002 | Tucker et al. | 424/423 |
| 6,485,723 B1 | 11/2002 | Badylak et al. | 424/93.7 |
| 2001/0049141 A1 | 12/2001 | Fike et al. | 435/384 |
| 2002/0064807 A1 | 5/2002 | Badylak et al. | 435/34 |
| 2002/0106394 A1 | 8/2002 | Tucker et al. | 424/423 |
| 2002/0188319 A1 | 12/2002 | Morris et al. | 606/213 |
| 2003/0068815 A1 | 4/2003 | Stone et al. | 435/325 |

OTHER PUBLICATIONS

Robert J. Woods, "Food Irradiation," Endeavor, New Series, vol. 18, No. 3, 1994, pp. 104–108.

A. Dziedzic–Goclawska et al., "Sterilisation of Tissue Allografts," Advances in Tissue Banking, vol. 1, pp. 261–321.

M.J. Goertzen et al., "Sterilisation of Canine Anterior Cruciate Allografts by Gamma Irradiation in Argon," Journal of Bone and Joint Surgery (Corrections), vol. 77–B, No. 2, Mar. 1995, pp. 205–212.

AABB FDA Liaison Meeting, ABC Newsletter, Dec. 12, 1997, pps. 14.

Tikvah Alper et al., The Exceptionally Small Size of the Scrapie Agent, 1966, pps. 278–284, Biochemical and Biophysical Research Communications, vol. 22, No. 3.

Tikvah Alper et al., Protection by Anoxia of the Scrapie Agent and Some DNA and RNA Viruses Irradiated as Dry Preparations, 1968, pps. 157–166, J. gen. Virol., vol. 3.

Tikvah Alper et al., Does the Agent of Scrapie Replicate Without Nucleic Acid! May 20, 1967, pps. 764–766, Nature, vol. 214.

Tikvah Alper et al., The Scrapie Agent: Evidence Against its Dependence For Replication on Intrinsic Nucleic Acid, 1978, pps. 503–516, J. gen. Virol., vol. 41.

Michael L. Baldwin et al., Irradiation of Blood Components, 1992, pps. 1–78, American Association of Blood Banks.

R.H. Bassin et al., Abrogation of $Fv-1^b$ Restriction With Murine Leukemia Viruses Inactivated by heat or by Gamma Irradiation, May 1978, pps. 306–315, Journal of Virology, vol. 26, No. 2.

Guy Beauregard et al., Temperature Dependence of the Radiation Inactivation of Proteins, 1985, pps. 117–120, Analytical Biochemistry, vol. 150.

David R. Brown et al., Antioxidant Activity Related to Copper Binding of Native Prion Protein, 2001, pps. 69–76, Journal of Neurochemistry, vol. 76.

P. Brown, The Risk of Blood–Borne Creutzfeldt–Jakob Disease, 1999, pps. 53–59, Advances in Transfusion Safety Dev. Biol. vol. 102.

P. Brown et al., Further Studies of Blood Infectivity in an Experimental Model of Transmissible Spongiform Encephalopathy, With an Explanation of Why Blood Components Do Not Transmit Creutzfeldt–Jakob Disease in Humans, Nov./Dec. 1999, pps. 1169–1178, Transfusion, vol. 39.

Paul Brown et al., Effect of Chemicals, Heat, and Histopathologic Processing on High–Infectivity Hamster––Adapted Scrapie Virus, May 1982, pps. 683–687, The Journal of Infectious Diseases, vol. 145, No. 5.

P. Brown et al., The Distribution of Infectivity in Blood Components and Plasma Derivatives in Experimental Models of Transmissible Spongiform Encephalopathy, Sep. 1998, pps. 810–816, Transfusion, vol. 38.

Derwent Publication AN—111469.

Derwent Publication—AN 2159557.

Derwent Publication—AN 2526936.

P. Di Simplicio et al., The Reactivity of the SH Group of Bovine Serum Albumin With Free Radicals, 1991, pps. 253–262, Free Rad. Res. Comms., vol. 14, No. 4.

Duane C. Eichler et al., Radiation Inactivation Analysis of Enzymes, Jul. 15, 1987, pps. 9433–9436, The Journal of Biological Chemistry, vol. 262, No. 20.

Luanne H. Elliott et al., Inactivation of Lassa, Marburg, and Ebola Viruses by Gamma Irradiation, Oct. 1982, pps 704–708, Journal of Clinical Microbiology, vol. 16, No. 4.

Fields et al., Susceptibility of Scrapie Agent to Ionizing Radiation, Apr. 5, 1969, pps. 90–91, Nature, vol. 222.

D.A. Haig, Further Studies on the Inactivation of the Scrapie Agent by Ultraviolet Light, 1969, pps. 455–457, J. gen. Virol., vol. 5.

H. Hiemstra et al., Inactivation of Human Immunodeficiency Virus by Gamma Radiation and its Effect on Plasma and Coagulation Factors, 1991, pps. 32–39, Transfusion, vol. 31, No. 1.

B. Horowitz et al., Inactivation of Viruses in Labile Blood Derivatives, II. Physical Methods, 1985, pps. 523–527, Transfusion, vol. 25, No. 6.

Carol House et al., Inactivation of Viral Agents in Bovine Serum by Gamma Irradiation, 1990, pps. 737–740, Can. J. Microbiol., vol. 36.

E.S. Kempner et al., Size Determination of Enzymes by Radiation Inactivation, 1979, pps. 2–10, Analytical Biochemistry, vol. 92.

J.D. Keathley et al., Is There Life After Irradiation? Part 2: Gamma–Irradiated FBS in Cell Culture, Jul./Aug. 1993, pps. 46–52, BioPharm.

A.D. Kitchen, Effect of Gamma Irradiation on the Human Immunodeficiency Virus and Human Coagulation Proteins, 1989, pps. 223–229, Vox Sang, vol. 56.

Raymond Latarjet, Inactivation of the Agents of Scrapie, Creutzfeldt–Jakob Disease, and Kuru by Radiations, 1979, pps. 387–407, Slow Transmissible Diseases of the Nervous System, vol. 2.

R. Latarjet et al., Inactivation of the Scrapie Agent by Near Monochromatic Ultraviolet Light, Sep. 26, 1970, pps. 1341–1343, Nature, vol. 227.

Douglas C. Lee et al., A Direct Relationship Between the Partitioning of the Pathogenic Prion Protein and Transmissible Spongiform Encephalopathy Infectivity During the Purification of Plasma Proteins, Apr. 2001, pps. 449–455, Transfusion, vol. 41.

Susan F. Leitman, Use of Blood Cell Irradiation in the Prevention of Posttransfusion Graft–vs–Host Disease, 1989, pps. 219–232, Transfus. Sci., vol. 10.

Linda Marton et al., Disinfection and Inactivation of the Human T. Lymphotrogic Virus Type III/Lymphadenopathy–Associated Virus, Aug. 1985, pps. 400–403,The Journal of Infectious Diseases, vol. 151, No. 2.

S.I. Miekka et al., New Methods for Inactivation of Lipid–enveloped and Non–enveloped Viruses, 1998, pps. 402–408, Haemophilia, vol. 4.

Z. Mark Plavsic et al., Resistance of Porcine Circovirus to Gamma Irradiation, Apr. 2001, pps. 32–36, BioPharm.

Pollard, The Effect of Ionizing Radiation of Viruses, pps. 65–71.

Elena Quaglio et al., Copper Converts the Cellular Prion Protein Into a Protease–resistant Species That Is Distinct From the Scrapie Isoform, Apr. 6, 2001, pps. 11432–11438, The Journal of Biological Chemistry, vol. 276, No. 14.

Brian D. Reid, The Sterways Process: a New Approach to Inactivating Viruses Using Gamma Radiation, 1998, pps. 125–130, Biologicals, vol. 26.

Robert G. Rohwer, Estimation of Scrapie Nucleic Acid MW From Standard Curves for Virus Sensitivity to Ionizing Radiation, Mar. 27, 1986, pp. 381, Nature, vol. 320, No. 6060.

Robert G. Rohwer, Scrapie Infectious Agent is Virus–like in Size and Susceptibility to Inactivation, Apr. 12, 1984, pps. 658–662, Nature, vol. 308.

R.G. Rohwer, The Scrapie Agent: "A Virus by Any Other Name", pps. 195–232, Current Topics In Microbiology and Immunology, vol. 172.

Robert G. Rohwer et al., Scrapie—Virus or Viroid, The Case For A Virus, pps. 333–355, Laboratory of Central Nervous System Studies, National Institutes of Neurological and Communicative Disorders and Stroke, National Institutes of Health.

Robert G. Rohwer, Virus–Like Sensitivity of the Scrapie Agent to heat Inactivation, Feb. 10, 1984, pps. 600–602, Science, vol. 223.

Robert Sullivan et al. Inactivation of Thirty Viruses by Gamma Radiation, Jul. 1971, pps. 61–65, Applied Microbiology, vol. 22, No. 1.

Boon–Seng Wong et al., Copper Refolding of Prion Protein, 2000, pps. 1217–124, Biochemical and Biophysical Research Communications, vol. 276.

Boon–Seng Wong et al., Differential Contribution of Superoxide Dismutase Activity by Prion Protein in Vivo, 2000, pps. 136–139, Biochemical and Biophysical Research Communications, vol. 273.

Boon–Seng Wong et al., Prion Disease: A Loss of Antioxidant Function? 2000, pps. 249–252, Biochemical and Biophysical Research Communications, vol. 275.

D.E. Wyatt et al., Is There Life After Irradiation? Part I: Inactivation of Biological Contaminants, Jun. 1993, pps. 34–39, BioPharm.

License Amendment and Procedures for Gamma Irradiation of blood Products, Jun. 22, 1993, pps. 1–18, Dept. of Health & Human Services, Food and Drug Administration.

M.F. Alladine et al., $\gamma$–Radiation Damage to Starr–Edwards Valves, Mar. 16, 1968, pp. 68, The Lancet, Letters to the Editor.

Ch. Baquey et al., Radiosteriliation of Albuminated Polyester Protheses, May 1987, pps. 185–189, Biomaterials, vol. 8.

Edward H. Bedrossian, Jr., HIV and Banked Fascia Lata, 1991, pps. 284–288, Ophthalmic Plastic and Reconstructive Surgery, vol. 7, No. 4.

Liu Bingci, Mouse Antibody Response Following Repetitive Injections of Gamma–Irradiated human Placenta Collagen, Jun. 1994, pps. 100–103, Chinese Medical Sciences Journal, vol. 9, No. 2.

E.A. Borisov et al., Protein Degradation During Interphase Death of Thymocytes Induced by Radiation and Dexamethasone, 1990, pps. 519–521.

R. G. Burwell, The Fate of Freeze–Dried Bone Allografts, Jun. 1976, pps. 95–111, Transplantation Proceedings, vol. VII, No. 2, Supplement 1.

L. Callegaro et al., Hollow Fiber Immobilized L–Asparaginase: In Vivo and In Vitro Immunological Studies, 1983, pps. 91–96, The International Journal of Artificial Organs, vol. 6, No. 2.

G. Campalani et al., Aortic Valve Replacement With Frozen Irradiated Homografts, 1989, pps. 558–561, Eur. J. Cardio-–thoracic Surgery, vol. 3.

David T. Cheung et al., The Effect of $\gamma$–Irradiation on Collagen Molecules, Isolated $\alpha$–chains, and Crosslinked Native Fibers, 1990, pps. 581–589, Journal of Biomedical Materials Research, vol. 24.

David J. Cohen et al., The Fate of Aortic Valve Homografts 12 to 17 Years After Implantation, Mar. 1988, pps 482–484, Chest, vol. 93, No. 3.

A.G. Chuchalin et al., Clinical Immunosorbents Basing on Space–Network Polymers, 1998, pps. 1524–1529, All Union Research Institute of Chemical Reagents and Chemicals of Special Purity, Moscow.

P. De Deyne et al., Some Effects of Gamma Irradiation on Patellar Tendon Allografts, 1991, pps. 51–62, Connective Tissue Research, vol. 27.

E.A. Dyskin et al., Hemomicrocirculatory Bed in the Wall of Hollow Organs of the Dog Gastrointestinal Tract at Portal Hypertension, pps. 68–73.

R. Guidoin et al., A Compounds Arterial Prosthesis: The Importance of the Sterilization Procedure on the Healing and Stability of Albuminated Polyester Grafts, Mar. 1985, pps. 122–128, Biomaterials, vol. 6.

Ph. Hernigou et al., Radiation Sterilization of Bone and the HIV Virus, 1993, pps. 445–451, Revue de Chirurgie Orthopedique, vol. 79.

Hsing–Wen Sung et al. Effects of Various Chemical Sterilization Methods on the Crosslinking and Enzymatic Degradation Characteristics of an Epoxy–Fixed Biological Tissue, Dec. 1996, pps. 376–383, Sterilization of Biological Tissues.

James R. Malm et al., An Evaluation of Aortic Valve Homografts Sterilized by Electron Beam Energy, Oct. 1967, pps. 471–477, Journal of Thoracic and Cardiovascular Surgery, vol. 54, No. 4.

James R. Malm et al., Results of Aortic Valve Replacement Utilizing Irradiated Valve Homografts, pps 740–747, Annals New York Academy of Sciences.

W. Oh et al., Mitral Valve Replacement With Preserved Cadaveric Aortic Homografts, May 1973, pps. 712–721, The Journal of Thoracic and Cardiovascular Surgery, vol. 65, No. 5.

K. Pietrucha, New Collagen Implant As Dural Substitute, Apr. 1991, pps. 320–323, Biomaterials, vol. 12.

Maria Raptopoulou–Gigi et al., Antimicrobial Proteins in Sterilised Human Milk, Jan. 1, 1977, pps. 12–14, British Medical Journal, vol. 1.

Edward A. Rittenhouuse et al., Sterilization of Aortic Valve Grafts for Transplantation, Jul. 1970, pps. 1–5, Aortic Valve Grafts for Transplantation, Archives of Surgery, vol. 101, No. 1.

H. Sato et al., Sterilization of Therapeutic Immunoadsorbents by Ionizing Radiation, 1986, pps. 131–136, The International Journal of Artificial Organs, vol. 9, No. 2.

Richard A. Smith et al., Gamma Irradiation of HIV–1, 2001, pps. 815–819, Journal of Orthopaedic Research, vol. 19.

Barbara Lüssi–Schlatter et al., Die Antimikrobielle Behandlung von Peroralen Enzympräparaten mit Gamma–Strahlen, Pharmazeutisches Institut der Eidgenössischen Technischen Hochschule Zürich Galenische Abteilung.

O. Cornu et al., Effect of Freeze–Drying and Gamma Irradiation on the Mechanical Properties of Human Cancellous Bone, 2000, pps. 426–431, Journal of Orthopaedic Research, vol. 18.

Anna Dziedzic–Goclawska et al., Effect of Radiation Sterilization on the Osteoinductive Properties and the Rate of Remodeling of Bone Implants Preserved by Lyophilization and Deep–Freezing, Nov. 1991, pps. 30–37, Clinical Orthopaedics and Related Research, No. 272.

Ole T. Jensen et al., Vertical Guided Bone–Graft Augmentation in a New Canine Mandibular Model, 1995, pps. 335–343, The International Journal of Oral and Maxillofacial Implants, vol. 10, No. 3.

Ronald W. Katz et al., Radiation–Sterilized Insoluble Collagenous Bone Matrix is a Functional Carrier of Osteogenin for Bone Induction, 1990, pps. 183–185, Calcified Tissue International, vol. 47.

Everard Munting et al., Effect of Sterilization on Osteoinduction; 1998, pps. 34–38, Acta Orthop Scand, vol. 59, No. 1.

P.A. Puolakkainen et al., The Effect of Sterilization on Transforming Growth Factor β Isolated From Demineralized Human Bone, 1993, pps. 679–685, Transfusion, vol. 33, No. 8.

U. Ripamonti et al., Long–Term Evaluation of Bone Formation by Osteogenic Protein 1 in the Baboon and Relative Efficacy of Boon–Derived Bone Morphogenetic Proteins Delivered by Irradiated Xenogeneic Collagenous Matrices, 2000, pps. 1798–1809, Journal of Bone and Mineral Research, vol. 15, No. 9.

A. Salehpour et al., Dose–Dependent Response of Gamma Irradiation on Mechanical Properties and Related Biochemical Composition of Goat Bone–Patellar Tendon–Bone Allografts, 1995, pps. 898–906, Journal of Orthopaedic Research, vol. 13.

Nikolaus Schwarz et al., Irradiation–sterilization of Rat Bone Matrix Gelatin, 1988, pps. 165–167, Acta Orthop Scand, vol. 59, No. 2.

C.W. Smith et al., Mechanical Properties of Tendons: Changes With Sterilization and Preservation, Feb. 1996, pps. 56–61, Journal of Biochemical Engineering, vol. 118.

Yukiyoshi Toritsuka et al., Effect of Freeze–Drying or γ–Irradiation on Remodeling of Tendon Allograft in a Rat Model, 1997, pps. 294–300, Journal of Orthopaedic Research, vol. 15.

Konrad Wangerin et al., Behavior of Differently Sterilized Allogenic Lyophilized Cartilage Implants in Dogs, 1987, pps. 236–242, J. Oral Maxillofac Surg, vol. 45.

S. Wientroub et al., Influence of Irradiation on the Osteoinductive Potential of Demineralized Bone Matrix, 1988, pps. 255–260, Calcified Tissue International, vol. 42.

Blanchy, B.B. et al., Immobilization of Factor VII on Collagen Membranes, J. Biomedical Materials Research, 20:469–479 (1986)(John Wiley & Sons, Inc.).

Boyer, T.D. et al., Radiation Inactivation of Microsomal Glutathione S–Transferase, The Journal of Biological Chemistry, 261:16963–16968 (1986).

Chanderkar, L.P. et al., The Involvement of Aromatic Amino Acids in Biological Activity of Bovine Fibrinogen as Assessed by Gamma–Irradiation, Radiation Research, 65:283–291 (1976) (Academic Press, Inc.).

Chanderkar, L.P. et al., Radiation–Induced Changes In Purified Prothrombin and Thrombin, Biochimica et Biophysica Acta, 706:1–8 (1982) (Elsevier Biomedical Press).

Chin, S. et al., Virucidal Treatment of Blood Protein Products With UVC Radiation, Photochemistry and Photobiology, 65:432–435 (1997) (American Society for Photobiology).

Ghosh, M.M. et al., A Comparison of Methodologies for the Preparation of Human Epidermal–Dermal Composites, Annals of Plastic Surgery; 39:390–404 (1997) (Lippincott–Raven Publishers).

Goertzen, M.J. et al., Anterior Cruciate Ligament Reconstruction Using Cryopreserved Irradiated Bone–ACL–Bone–Allograft Transplants, Knee Surg. Sports Traumatol. Arthroscopy, 2:150–157 (1994) (Springer–Verlag).

Hsiue, G. et al., Absorbable Sandwich–Like Membrane for Retinal–Sheet Transplantation, pp. 20–25 (2002) (Wiley Periodicals, Inc).

Jensen, J. et al., Membrane–bound Na, K–ATPase: Target Size and Radiation Inactivation Size of Some of Its Enaymatic Reactions, J. Biological Chemistry, 263:18063–18070 (1988) (Am. Soc. for Biochem. and Mol. Biol.).

Kamat, H.N. et al., Correlation of Structrual Alterations in Bovine Fibrinogen with Loss of Clotting Properties After Gamma Irradiation, Radiation Research, 49:381–389 (1972) (Academic Press, Inc.).

Kempner, E.S. et al., Effect of Environmental Conditions on Radiation Target Size Analyses, Analytical Biochemistry, 216:451–455 (1994).

Kempner, E.S. et al., Radiation–Damaged Tyrosinase Molecules are Inactive, Biophysical Journal, 55:159–162 (1989) (Biophysical Society).

Kuijpers, A.J. et al., In vivo Compatibility and Degradation of Crosslinked Gelatin Gels Incorporated in Knitted Dacron, pp. 137–144 (2000) (John Wiley & Sons, Inc.).

Le Maire, M. et al., Effects of Ionizing Radiations on Proteins, Journal of Biochem., 267:431–439 (1990).

Ma, J.T. et al., Functional Size Analysis of F–ATPase from *Escherichia coli* by Radiation Inactivation, The Journal of Biological Chemistry, 268:10802–10807 (1993) (The Am. Soc. for Biochem. and Mol. Bio., Inc.).

Marx, G. Protecting Fibrinogen with Rutin During UVC Irradiation for Viral Inactivation, Photochemistry and Photobiology, 63:541–546 (1996) (American Society for Photobiology).

Nagrani, S. et al., The Radiation–Induced Inactivation of External Yeast Invertase in Dilute Aqueous Solution, Int. J. Radiat. Biol., 55:191–200 (1989) (Taylor & Francis Ltd.).

Nielsen, M. et al., The Apparent Target Size of Rat Brain Benzodiazepine Receptor, Acetylcholinesterase, and Pyruvate Kinase Is Highly Influenced by Experimental Conditions, The Journal of Biological Chemistry, 263:11900–11906 (1988) (The American Society for Biochemistry and Molecular Biology, Inc.).

Potier, M. et al., Radiation Inactivation of Proteins: Temperature–Dependent Inter–Protomeric Energy Transfer in Ox Liver Catalase, Biochem. J., 298:571–574 (1994).

Sakai, T. et al., Microbiological Studies on Drugs and Their Raw Materials. IV. Sterilization of Microbial Contaminants in Enzyme Powder by Gamma Irradiation, Chem. Pharm. Bull., 26:1130–1134 (1978).

Salim–Hanna, M. et al., Free Radical Scavenging Activity Of Carnosine, Free Rad. Res. Comms., 14:263–270 (1991) (Harwood Academic Publishers GmbH).

Song, K.B. et al., Effect of Gamma–irradiation on the Physicochemical Properties of Blood Plasma Proteins, 2002 Annual Meeting and Food Expo–Anaheim, California, Session 30C–1, Food and Chemistry: Proteins, (Jun. 2002) (Abstract).

Suomela, H., Inactivation of Viruses in Blood and Plasma Products, Transfusion Medicine Reviews, 7:42–57 (1993) (W.B. Saunders Company).

(Abstract of EP0919198A2 and EP0919198A3 (Delphion–DERABS Abstract # G1999–304614)).

Website: www.wslfweb.org/docs/dstp2000.dtopdf/19–MD.pdf (Defense Science and Technology Plans, (Feb. 2000) p. 176, Section II, MD.03, U.S. Department of Defense Deputy Under Secretary of Defense (Science and Technology)).

Website: www.usacc.org/ataccc/ppt.html, (Advanced Technology Applications for Combat Casualty Care, 2001 Presentations, US Army Medical Research and Material Command Combat Casualty Care Research Program (2001)).

Website: www.usacc.org/RevisedStepB.html, Bakaltcheva, I. et al., (FY01 Request for Proposals–Intramural–Revised 2, Combat Casualty Care Research Program, (2002)).

Website: www.benvue.com/history/history_content.html, (2002).

Website: www.phase–technologies.com/html/vol.2no1.html, Jennings, T.A., (Glossary of Terms for Lyophilization) (1999).

Website: www.phase–technologies.com/html/vol.1no9.html, Jennings, T.A., (Overview of the Lyophilization Process) (1998).

Website: www.phase–technologies.com/html/vol.1no2.html, Jennings, T.A., (Role of Product Temperature in the Lyophilization Process) (1998).

Website: www.phase–technologies.com/html/vol.2no2.html, Jennings, T.A., (What I Wish I Knew About Lyophilization) (1999).

Website: www.phase–technologies.com/html/vol.1no7.html, Jennings, T.A., (Which Shelf Temperature During Lyophilization) (1998).

Website: www.phase–technologies.com/html/vol.1no10.html, Jennings, T.A., (Yes, You have no Eutectic) (1998).

* cited by examiner

Gamma Irradiation of a Galactosidase in the Absence or Presence of Ascorbate Alone or in Combination with Gly-Gly

METHODS FOR STERILIZING PREPARATIONS OF GLYCOSIDASES

BACKGROUND OF THE INVENTION

1. Field of the Invention

The present invention relates to methods for sterilizing preparations of glycosidases to reduce the level therein of one or more active biological contaminants or pathogens, such as viruses, bacteria (including inter- and intracellular bacteria, such as mycoplasmas, ureaplasmas, nanobacteria, chlamydia, rickettsias), yeasts, molds, fungi, prions or similar agents responsible, alone or in combination, for TSEs and/or single or multicellular parasites. The present invention particularly relates to methods of sterilizing preparations of glycosidases, such as alpha-glucosidase or alpha-galactosidase, with irradiation.

2. Background of the Related Art

The principal foods upon which an organism, such as a human, survives can be broadly categorized as carbohydrates, fats and proteins. These substances, however, are useless as nutrients without the process of digestion to break down foods into chemical components that are sufficiently small to be absorbable in the digestive tract.

Digestion of carbohydrates begins in the mouth and stomach. Saliva contains the enzyme ptyalin (an alpha-amylase), which hydrolyses starch into maltose and other small polymers of glucose. The pancreatic alpha-amylase is similar to the salivary ptyalin, but several times as powerful. Therefore, soon after chyme empties into the duodenum and mixes with pancreatic juice, virtually all of the starches are converted into disaccharides and small glucose polymers. These disaccharides and small glucose polymers are hydrolysed into monosaccharides by intestinal epithelial enzymes, such as intestinal sucrase, intestinal maltase, and intestinal lactase.

Digestion of proteins begins in the stomach. The ability of pepsin to digest collagen is especially important because collagen is a major constituent of the intercellular connective tissue of meats. For other glycosidases to penetrate meats and digest various cellular proteins, the collagen fibers must first be partially digested by pepsin. People who lack peptic activity in the stomach will experience poor absorption of ingested meats because there is poor penetration by these other glycosidases.

Most protein digestion results from the actions of the pancreatic proteolytic enzymes. Proteins leave the stomach in the form of proteoses, peptones and large polypeptides, and are digested into dipeptides, tripeptides and the like by pancreatic proteolytic enzymes or polypeptidases. Trypsin and chymotrypsin split protein molecules into smaller polypeptides at specific peptide linkages, whereas carboxy-polypeptidase cleaves amino acids from the carboxyl ends of polypeptides. The zymogen proelastase is converted to the active protease elastase, which in turn digests elastin fibers that hold together most meat.

Further digestion of polypeptides takes place in the intestinal lumen. Aminopolypeptidase and several other polypeptidases split large polypeptides into dipeptides, tripeptides and amino acids, which are then transported into enterocytes that line the intestinal villi. Inside the enterocytes, other polypeptidases split any remaining peptides into their constituent amino acids, which then enter the blood.

Digestion of fats first requires emulsification by bile acids and lecithin, which increase the surface area of the fats up to 1000-fold. Because lipases are water-soluble glycosidases that can bind only on the surface of a fat globule, this emulsification process is important for the complete digestion of fat. The most important glycosidase in the digestion of triglycerides is pancreatic lipase, which breaks these down into free fatty acids and 2-monoglycerides. After these free fatty acids and monoglycerides enter the enterocytes, they are generally recombined into new triglyerides. A few monoglycerides, however, are further digested by intracellular lipases into free fatty acids.

Glycosidases are required to digest or break down saccharide units (usually polysaccharides). For example, glycosidases are required to digest or breakdown the saccharide untis that are covalently attached to proteins so that proteases can then gain access to the protein for cleavage of the individual amino acids therefrom, to thereby promote absorption of the resulting amino acids.

A number of glycosidases are present in the human gastrointestinal tract, but, to date, only some have been isolated and sufficiently characterized. Many glycosidases, however, have been isolated and characterized from plant and microbial sources, which, to some extent, has provided a roadmap for studies of animal glycosidases. Thus, glycosidases are known that cleave and remove O-linked sugar units from glycoproteins, and from glycolipids and polysaccharides, for example, alpha-N-acelylgalactosaminidase. Other glycosidases include N-acetylneuraminic acid aldolase, beta(1-4) galactosidase, beta(1-3,6) galactosidase, beta(1-3,4,6) galactosidase, beta (1-6)galactosidase, alpha(1-3,6) galactosidase, beta-glucosaminidase, alpha-mannosidase, alpha(1-3,4) fucosidase, alpha(1-2,3,4) fucosidase, alpha(1-2) fucosidase, beta(1-2) xylosidase, beta(1-4) xylosidase, peptide-$N^4$-(acetyl-beta-glucosaminyl)-asparagine amidase (EC 3.5.1.52) hexosaminidase, beta-N-acetylhexosaminidase, alpha(2-3,6,8,9) neuraminidase, various sialidases, such as N-acetylneuraminate glycohydrolase (EC 3.2.1.18), various glycoamidases, alpha-mannosidase, and beta-mannosidase.

The nomenclature of glycosidases typically indicates the type of linkages that are cleaved by the enzyme. For example, beta(1-3,6) galactosidase cleaves only beta(1-3,6) galactose linkages, but not beta(1-4) galactose linkages.

Reaction conditions and substrate specificities vary greatly, depending on the particular glycosidase. For example, a given glycosidase may be ineffective when sialic acid is present on N-linked oligosaccharides. The optimal pH activities of glycosidases also vary according to the particular glycosidase, with some being optimally active at acidic pH values, others at values near neutral pH, and yet others at alkaline pH values.

Preparations of glycosidases may be required for administration to humans and other animals when, for example, there is a genetically caused disease, such as lack of endogenous glycosidases, or lack of active glycosidases. One genetic disease characterized by a partially or completely inactive glycosidase is Fabry disease, which afflicts about one in 40,000 people in the United States. Fabry disease is an X-linked lysosomal disorder in which the patient's body does not have a normal ability to break down a fatty substance, globotriaosylceramide (also known as $Gb_3$ or ceramidetrihexoside). $Gb_3$ is present in membranes of many cell types, including the membranes of red blood cells. Roughly 1% of one's red blood cells are replaced each day, which means that a significant amount of $Gb_3$ requires degradation each day.

One of the major lysosomal enzymes involved in the degradation of $Gb_3$ is alpha-galactosidase A ("α-gal A"), which is either partially or completely inactive in patients with Fabry disease. As a result, $Gb_3$ accumulates in lysosomes throughout the patient's body, which impairs (clogs blood vessels with built-up $Gb_3$) organs and body parts that depend on proper functioning of small blood vessels, such as kidneys, heart, nervous system, and skin.

The most common symptom of Fabry disease is pain, which may occur in the form of periods of intense burning, or sharp, shooting pain. The pain may be brought on by such events as exercise, fever, fatigue, stress, and/or exposure to temperature changes. In addition, many patients with Fabry disease are unable to perspire, which causes further discomfort with exercise or exposure to high temperatures. Periods of pain are most common in childhood, but also may not present until the 20s, when sufficient $Gb_3$ has accumulated. In some patients, the pain subsides with increasing age, and in others the pain increases.

Another common symptom of Fabry disease is a spotted, dark-red skin rash that most commonly occurs from the belly button down to about the knees (the "bathing trunk" rash). Other symptoms that can be associated with Fabry disease, and that can exhibit extremes in variability from patient to patient, include chronic bronchitis and shortness of breath, swelling of the legs, diarrhea, osteoporosis, growth retardation, delayed puberty, and development of a hazy or opaque cornea.

Once the buildup of $Gb_3$ reaches a critical level, symptoms begin to appear more regularly, typically including problems with function of the heart, the circulatory system, and the kidneys. Thus, common problems include heart and circulatory malfunctions, such as high blood pressure, heart attack, heart failure, mitral valve prolapse, cardiac arrhythmia, stroke, and kidney malfunctions, such as renal failure requiring dialysis of the patient.

Recently, treatment for Fabry disease has included infusion of a preparation of α-galactosidase A (Replagal) to patients, with reported stabilization or improvement in renal function, decreased pain, and reduction in mass of the heart (Schiffmann, et al., "Enzyme Replacement Therapy in Fabry Disease: A Randomized Controlled Trial." *JAMA*, Jun. 6, 2001, Vol.285, No. 21, pp. 2743_2749.).

Another genetic disease characterized by inactive glycosidases is Glycogen Storage Disease Type II (also called GSD II, acid maltase deficiency, AMD, Pompe disease, and alpha-glucosidase deficiency), in which an autosomal recessive mutation is expressed for the lysosomal enzyme acid alpha-glucosidase (acid maltase). Although prognosis and specific symptomology vary according to the subtype (infantile form [type a], childhood form [type b], or adult form [type c]), some of the general effects are roughly the same across the various types, in particular, respiratory and cardiac failure due to massive accumulations of glycogen in the respiratory muscles and in the heart itself. Other possible symptoms include muscle weakness and degeneration, and enlargement of the heart, liver and tongue. Normally, acid alpha-glucosidase breaks down excess glycogen in a cell; however, this function is blocked in cells of the GSD II patient to produce abnormal, excess accumulation of glycogen, which causes the muscle failure in respiratory muscles and in heart muscle. At least one report (H. Van den Hout, et al., 2000. "Recombinant human alpha-glucosidase from rabbit milk in Pompe patients." *Lancet* 356: 397–398 Jul. 29, 2000 issue)) has shown successful treatment of infantile GSD II patients with administration of recombinant human acid alpha-glucosidase.

Another medical use for glycosidases commonly occurs in response to gas (flatulence) that is caused by the human digestive tract's inability to degrade small disaccharides, trisaccharides, etc. These small oligosaccharides are then fermented by intestinal flora to produce undesired, excess gas. Such offending oligosaccharides are prevalent in cruciferous vegetables, such as broccoli, cabbage, cauliflower, and brussels sprouts, as well as in beans and lentils. Removal of the offending oligosaccharides in beans and lentils may be effected by bringing them to a boil to break the outer husks, adding a small quantity of baking soda (sodium bicarbonate) and turning off the heat, allowing the "brew" to sit for 4–8 hours, and thoroughly rinsing the resulting mixture several times with fresh tap water prior to completion of the cooking process. A simpler solution, however, involves administration of products containing alpha-galactosidase, such as Beano™, concurrently with consumption of a gas-producing food. These products decrease gas production by breaking down the oligosaccharides prior to their reaching intestinal fermenting sites, but do not degrade fiber molecules.

Preparations of glycosidases that are prepared for human, veterinary, diagnostic and/or experimental use may, however, contain unwanted and potentially dangerous biologically active contaminants or pathogens, such as viruses, bacteria (including inter- and intracellular bacteria, such as mycoplasmas, ureaplasmas, nanobacteria, chlamydia, rickettsias), yeasts, molds, fungi, single or multicellular parasites, prions or similar agents responsible, alone or in combination, for TSEs. Consequently, it is of utmost importance that any biologically active contaminant or pathogen in the preparation be inactivated before the product is used. This is especially critical when the glycosidase preparation is to be administered directly to a patient, for example in human therapy. This is also critical for the various enzyme preparations that are prepared in media which contain various types of plasma and/or plasma derivatives or other biologic materials and which may contain prions, bacteria, viruses and other biological contaminants or pathogens.

Most procedures for producing preparations of enzymes have involved methods that screen or test the preparation for one or more particular biological contaminants or pathogens rather than removal or inactivation of the contaminant(s) and/or pathogen(s) from the preparation. Preparations that test positive for a biological contaminant or pathogen are merely not used. Examples of screening procedures include the testing for a particular virus in human blood from blood donors. Such procedures, however, are not always reliable and are not able to detect the presence of certain viruses, particularly in very low numbers, and in the case of as yet unknown viruses or other contaminants or pathogens that may be in blood. This reduces the value or certainty of the test in view of the consequences associated with a false negative result. False negative results can be life threatening in certain cases, for example in the case of Acquired Immune Deficiency Syndrome (AIDS). Furthermore, in some instances it can take weeks, if not months, to determine whether or not the preparation is contaminated. Moreover, to date, there is no reliable test or assay for identifying prions within a biological material that is suitable for screening out potential donors or infected material. This serves to heighten the need for an effective means of destroying prions within a biological material, while still retaining the desired activity of that material. Therefore, it would be desirable to apply techniques that would kill or inactivate biological contaminants and pathogens during and/or after manufacturing the preparation of glycosdisases.

The importance of these techniques is apparent regardless of the source of the biological material. All living cells and multi-cellular organisms can be infected with viruses and other pathogens. Thus the products of unicellular natural or recombinant organisms or tissues carry a risk of pathogen contamination. In addition to the risk that the producing cells or cell cultures may be infected, the processing of these and other biological materials creates opportunities for environmental contamination. The risks of infection are more apparent for multicellular natural and recombinant organisms, such as transgenic animals. Interestingly, even products from species as different from humans as transgenic plants carry risks, both due to processing contamination as described above, and from environmental contamination in the growing facilities, which may be contaminated by pathogens from the environment or infected organisms that co-inhabit the facility along with the desired plants. For example, a crop of transgenic corn grown out of doors, could be expected to be exposed to rodents such as mice during the growing season. Mice can harbour serious human pathogens such as the frequently fatal Hanta virus. Since these animals would be undetectable in the growing crop, viruses shed by the animals could be carried into the transgenic material at harvest. Indeed, such rodents are notoriously difficult to control, and may gain access to a crop during sowing, growth, harvest or storage. Likewise, contamination from overflying or perching birds has to potential to transmit such serious pathogens as the causative agent for psittacosis. Thus any biological material, regardless of its source, may harbour serious pathogens that must be removed or inactivated prior to the administration of the material to a reicipient.

In conducting experiments to determine the ability of technologies to inactivate viruses, the actual viruses of concern are seldom utilized. This is a result of safety concerns for the workers conducting the tests, and the difficulty and expense associated with the containment facilities and waste disposal. In their place, model viruses of the same family and class are used. In general, it is acknowledged that the most difficult viruses to inactivate are those with an outer shell made up of proteins, and that among these, the most difficult to inactivate are those of the smallest size. This has been shown to be true for gamma irradiation and most other forms of radiation as these viruses' diminutive size is associated with a small genome. The magnitude of direct effects of radiation upon a molecule are directly proportional to the size of the molecule, that is the larger the target molecule, the greater the effect. As a corollary, it has been shown for gamma-irradiation that the smaller the viral genome, the higher the radiation dose required to inactive it.

Among the viruses that may contaminate both human and animal-derived preparations, the smallest, and thus most difficult to inactivate, belong to the family of Parvoviruses and the slightly larger protein-coated Hepatitis virus. In humans, the Parvovirus B19, and Hepatitis A are the agents of concern. In porcine-derived materials, the smallest corresponding virus is Porcine Parvovirus. Since this virus is harmless to humans, it is frequently chosen as a model virus for the human B19 Parvovirus. The demonstration of inactivation of this model parvovirus is considered adequate proof that the method employed will kill human B19 virus and Hepatitis A, and by extension, that it will also kill the larger and less hardy viruses such as HIV, CMV, Hepatitis B and C and others.

More recent efforts have focussed on methods to remove or inactivate contaminants in the products. Such methods include heat treating, filtration and the addition of chemical inactivants or sensitizers to the product.

Heat treatment requires that the product be heated to approximately 60° C. for about 70 hours which can be damaging to sensitive products. In some instances, heat inactivation can actually destroy 50% or more of the biological activity of the product.

Filtration involves filtering the product in order to physically remove contaminants. Unfortunately, this method may also remove products that have a high molecular weight. Further, in certain cases, small viruses and similarly sized contaminants and pathogens, such as prions, may not be removed by the filter.

The procedure of chemical sensitization involves the addition of noxious agents which bind to the DNA/RNA of the virus and which are activated either by UV or other radiation. This radiation produces reactive intermediates and/or free radicals which bind to the DNA/RNA of the virus, break the chemical bonds in the backbone of the DNA/RNA, and/or cross-link or complex it in such a way that the virus can no longer replicate. This procedure requires that unbound sensitizer is washed from products since the sensitizers are toxic, if not mutagenic or carcinogenic, and cannot be administered to a patient.

Irradiating a product with gamma radiation is another method of sterilizing a product. Gamma radiation is effective in destroying viruses and bacteria when given in high total doses (Keathly et al., "Is There Life After Irradiation? Part 2," *BioPharm* July–August, 1993, and Leitman, Use of Blood Cell Irradiation in the Prevention of Post Transfusion Graft-vs-Host Disease," *Transfusion Science* 10:219–239 (1989)). The published literature in this area, however, teaches that gamma radiation can be damaging to radiation sensitive products, such as blood, blood products, enzymes, protein and protein-containing products. In particular, it has been shown that high radiation doses are injurious to red cells, platelets and granulocytes (Leitman). U.S. Pat. No. 4,620,908 discloses that protein products must be frozen prior to irradiation in order to maintain the viability of the protein product. This patent concludes that "[i]f the gamma irradiation were applied while the protein material was at, for example, ambient temperature, the material would be also completely destroyed, that is the activity of the material would be rendered so low as to be virtually ineffective". Unfortunately, many sensitive biological materials, such as monoclonal antibodies or enzymes, may lose viability and activity if subjected to freezing for irradiation purposes and then thawing prior to administration to a patient.

In view of the difficulties discussed above, there remains a need for methods of sterilizing preparations of one or more glycosidases that are effective for reducing the level of active biological contaminants or pathogens without an adverse effect on the preparation.

The above references are incorporated by reference herein where appropriate for appropriate teachings of additional or alternative details, features and/or technical background.

SUMMARY OF THE INVENTION

An object of the invention is to solve at least the above problems and/or disadvantages and to provide at least the advantages described hereinafter.

Accordingly, it is an object of the present invention to provide methods of sterilizing preparations of glycosidases by reducing the level of active biological contaminants or pathogens without adversely affecting the preparation. Other objects, features and advantages of the present invention will be set forth in the detailed description of preferred embodiments that follows, and in part will be apparent from the description or may be learned by practice of the invention. These objects and advantages of the invention will be realized and attained by the compositions and methods particularly pointed out in the written description and claims hereof.

In accordance with these and other objects, a first embodiment of the present invention is directed to a method for sterilizing a preparation of one or more glycosidases that is sensitive to radiation comprising irradiating the preparation of one or more glycosidases with radiation for a time effective to sterilize the material at a rate effective to sterilize the material and to protect the material from radiation.

Another embodiment of the present invention is directed to a method for sterilizing a preparation of one or more glycosidases that is sensitive to radiation comprising: (i) adding to a preparation of one or more glycosidases at least one stabilizer in an amount effective to protect the preparation of one or more glycosidases from radiation; and (ii) irradiating the preparation of one or more glycosidases with radiation at an effective rate for a time effective to sterilize the material.

Another embodiment of the present invention is directed to a method for sterilizing a preparation of one or more glycosidases that is sensitive to radiation comprising: (i) reducing the residual solvent content of a preparation of one or more glycosidases to a level effective to protect the preparation of one or more glycosidases from radiation; and (ii) irradiating the preparation of one or more glycosidases with radiation at an effective rate for a time effective to sterilize the preparation of one or more glycosidases.

Another embodiment of the present invention is directed to a method for sterilizing a preparation of one or more glycosidases that is sensitive to radiation comprising: (i) reducing the temperature of a preparation of one or more glycosidases to a level effective to protect the preparation of one or more glycosidases from radiation; and (ii) irradiating the preparation of one or more glycosidases with radiation at an effective rate for a time effective to sterilize the preparation of one or more glycosidases.

Another embodiment of the present invention is directed to a method for sterilizing a preparation of one or more glycosidases that is sensitive to radiation comprising: (i) applying to the preparation of one or more glycosidases a stabilizing process selected from the group consisting of: (a) reducing the residual solvent content of a preparation of one or more glycosidases, (b) adding to the preparation of one or more glycosidases at least one stabilizer, and (c) reducing the temperature of the preparation of one or more glycosidases; and (ii) irradiating the preparation of one or more glycosidases with radiation at an effective rate for a time effective to sterilize the preparation of one or more glycosidases, wherein the stabilizing process and the rate of irradiation are together effective to protect the preparation of one or more glycosidases from radiation.

Another embodiment of the present invention is directed to a method for sterilizing a preparation of one or more glycosidases that is sensitive to radiation comprising: (i) applying to the preparation of one or more glycosidases at least two stabilizing processes selected from the group consisting of: (a) reducing the residual solvent content of a preparation of one or more glycosidases, (b) adding to the preparation of one or more glycosidases at least one stabilizer, and (c) reducing the temperature of the preparation of one or more glycosidases; and (ii) irradiating the preparation of one or more glycosidases with radiation at an effective rate for a time effective to sterilize the preparation of one or more glycosidases, wherein the stabilizing processes may be performed in any order and are together effective to protect the preparation of one or more glycosidases from radiation.

The invention also provides a biological composition comprising at least one preparation of one or more glycosidases and a least one stabilizer in an amount effective to preserve the preparation of one or more glycosidases for its intended use following sterilization with radiation.

The invention also provides a biological composition comprising at least one preparation of one or more glycosidases in which the residual solvent content has been reduced to a level effective to preserve the preparation of one or more glycosidases for its intended use following sterilization with radiation.

The invention also provides a biological composition comprising at least one preparation of one or more glycosidases and at least one stabilizer in which the residual solvent content has been reduced and wherein the amount of stabilizer and level of residual solvent content are together effective to preserve the preparation of one or more glycosidases for its intended use following sterilization with radiation.

The invention also provides a biological composition comprising at least one preparation of one or more glycosidases wherein the total protein concentration of the preparation is effective to preserve the preparation of one or more glycosidases for its intended use following sterilization with radiation.

The invention also provides a method of treating a disease, disorder or deficiency of glycosidase comprising the administration of at least one preparation of one or more glycosidases that has been sterilized by one or more of the methods described herein that is effective to preserve the preparation for its intended use following sterilization with radiation.

Additional advantages, objects, and features of the invention will be set forth in part in the description which follows and in part will become apparent to those having ordinary skill in the art upon examination of the following or may be learned from practice of the invention. The objects and advantages of the invention may be realized and attained as particularly pointed out in the appended claims.

BRIEF DESCRIPTION OF THE DRAWINGS

The invention will be described in detail with reference to the following drawings in which like reference numerals refer to like elements wherein.

DETAILED DESCRIPTION OF PREFERRED EMBODIMENTS

A. Definitions

Figure 1A:
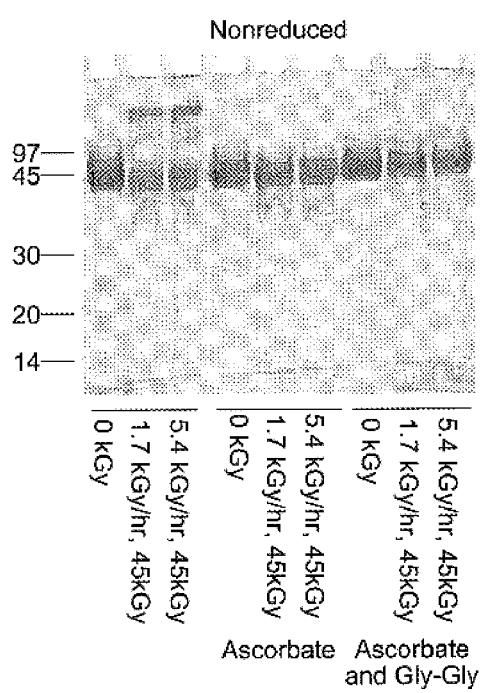
FIGS. 1A–1B are gels showing the protective effect of ascorbate (200 mM) and a combination of ascorbate (200 mM) and Gly—Gly (200 mM) on a frozen glycosidase preparation.

Unless defined otherwise, all technical and scientific terms used herein are intended to have the same meaning as is commonly understood by one of ordinary skill in the relevant art.

As used herein, the singular forms "a," "an," and "the" include the plural reference unless the context clearly dictates otherwise.

As used herein, the term "preparation of one or more glycosidases" is intended to mean any preparation derived or obtained from a living organism that contains one or more enzymes which can cleave a glycosidic bond, either alone or in combination with one or more additional enzymes or other compounds, and includes both endoglycosidases and exoglycosidases. Illustrative examples of glycosidases include, but are not limited to, the following: aldolases, such as N-acetylneuraminic acid aldolase; galactosidases, including alpha-galactosidases, such as alpha-galactosidase A and alpha (1-3,6) galactosidase, and beta-galactosidases, such as beta(1-4) galactosidase, beta(1-3,6) galactosidase, beta(1-3, 4,6) galactosidase and beta(1-6) galactosidase; mannosidases, such as alpha-mannosidase and beta-mannosidase; fucosidases, such as alpha(1-3,4) fucosidase, alpha(1-2,3,4) fucosidase, and alpha(1-2) fucosidase; xylosidases, such as beta(1-2) xylosidase and beta(1-4) xylosidase; aminidases, such as alpha-N-acelylgalactosaminidase, peptide-$N^4$-(acetyl-beta-glucosaminyl)-asparagine aminidase (EC 3.5.1.52), hexosaminidase, beta-N-acetylhexosaminidase, alpha(2-3,6, 8,9) neuraminidase; and sialidases, such as N-acetylneuraminate glycohydrolase (EC 3.2.1.18).

As used herein, the term "sterilize" is intended to mean a reduction in the level of at least one active biological contaminant or pathogen found in the preparation being treated according to the present invention.

As used herein, the term "biological contaminant or pathogen" is intended to mean a contaminant or pathogen that, upon direct or indirect contact with a preparation of one or more glycosidases, may have a deleterious effect on the enzyme(s) or upon a recipient thereof. Such biological contaminants or pathogens include the various viruses, molds, yeasts, bacteria and parasites known to those of skill in the art to generally be found in or infect preparations of glycosidases. Examples of biological contaminants or pathogens include, but are not limited to, the following: viruses, such as human immunodeficiency viruses and other retroviruses, herpes viruses, filoviruses, circoviruses, paramyxoviruses, cytomegaloviruses, hepatitis viruses (including hepatitis A, B and C), pox viruses, toga viruses, Epstein-Barr viruses and parvoviruses; bacteria, such as Escherichia, Bacillus, Campylobacter, Streptococcus and Staphalococcus; nanobacteria; parasites, such as Trypanosoma and malarial parasites, including Plasmodium species; yeasts; molds; mycoplasmas and ureaplasmas; chlamydia; rickettsias, such as *Coxiella burnetti*; and prions and similar agents responsible, alone or in combination, for one or more of the disease states known as transmissible spongiform encephalopathies (TSEs) in mammals, such as scrapie, transmissible mink encephalopathy, chronic wasting disease (generally observed in mule deer and elk), feline spongiform encephalopathy, bovine spongiform encephalopathy (mad cow disease); Creutzfeld-Jakob disease (including variant or new variant CJD), Fatal Familial Insomnia; Gerstmann-Straeussler-Scheinker syndrome; kuru; and Alpers syndrome. As used herein, the term "active biological contaminant or pathogen" is intended to mean a biological contaminant or pathogen that is capable of causing a deleterious effect, either alone or in combination with another factor, such as a second biological contaminant or pathogen or a native protein (wild-type or mutant) or antibody, in the preparation of one or more glycosidases and/or a recipient thereof.

As used herein, the term "a biologically compatible solution" is intended to mean a solution to which a preparation of one or more glycosidases may be exposed, such as by being suspended or dissolved therein, and remain viable, i.e., retain its essential biological, pharmacological, and physiological characteristics.

As used herein, the term "a biologically compatible buffered solution" is intended to mean a biologically compatible solution having pH and/or osmotic properties (e.g., tonicity, osmolality, and/or oncotic pressure) suitable for maintaining the integrity of the material(s) thereof, including suitable for maintaining essential biological, pharmacological, and physiological characteristics of the material(s) therein. Suitable biologically compatible buffered solutions typically have a pH between about 2 and about 8.5, and are isotonic or only moderately hypotonic or hypertonic. Biologically compatible buffered solutions are known and readily available to those of skill in the art.

As used herein, the term "stabilizer" is intended to mean a compound or material that reduces damage to the preparation being irradiated to a level that is insufficient to preclude the safe and effective use of the preparation. Illustrative examples of stabilizers include, but are not limited to, the following, including structural analogs and derivatives thereof: antioxidants; free radical scavengers, including spin traps, such as tert-butyl-nitrosobutane (tNB), α-phenyl-tert-butylnitrone (PBN), 5,5-dimethylpyrroline-N-oxide (DMPO), tert-butylnitrosobenzene (BNB), α-(4-pyridyl-1-oxide)-N-tert-butylnitrone (4-POBN) and 3,5-dibromo-4-nitroso-benzenesulphonic acid (DBNBS); combination stabilizers, i.e., stabilizers that are effective at quenching both Type I and Type II photodynamic reactions; and ligands, ligand analogs, substrates, substrate analogs, modulators, modulator analogs, stereoisomers, inhibitors, and inhibitor analogs. Preferred examples of stabilizers include, but are not limited to, the following: fatty acids, including 6,8-dimercapto-octanoic acid (lipoic acid) and its derivatives and analogs (e.g., alpha, beta, dihydro, bisno and tetranor lipoic acid), thioctic acid, 6,8-dimercapto-octanoic acid, dihydrolopoate (DL-6,8-dithioloctanoic acid methyl ester), lipoamide, bisonor methyl ester and tetranor-dihydrolipoic acid, omega-3 fatty acids, omega-6 fatty acids, omega-9 fatty acids, furan fatty acids, oleic, linoleic, linolenic, arachidonic, eicosapentaenoic (EPA), docosahexaenoic (DHA) and palmitic acids, and their salts and derivatives; flavonoids, phenylpropanoids, and flavonols, such as quercetin, rutin and its derivatives, apigenin, aminoflavone, catechin, hesperidin and naringin; carotenes, including alpha-, beta-, and gamma-carotenes; Co-Q10; xanthophylls; polyhydric alcohols, such as glycerol, mannitol, inositol, and sorbitol; sugars, including derivatives and stereoisomers thereof, such as xylose, glucose, ribose, mannose, fructose, erythrose, threose, idose, arabinose, lyxose, galactose, allose, altrose, gulose, talose, and trehalose; amino acids and derivatives thereof, including both D- and L-forms and mixtures thereof, such as arginine, lysine, alanine, valine, leucine, isoleucine, proline, phenylalanine, glycine, serine, threonine, methionine, cysteine, tyrosine, asparagine, glutamine, aspartic acid, histidine, N-acetylcysteine (NAC), glutamic acid, tryptophan, and sodium capryl N-acetyl tryptophan; azides, such as sodium azide; enzymes, such as Superoxide Dismutase (SOD), Catalase, and $\Delta^4$, $\Delta^5$ and $\Delta^6$ desaturases; uric acid and its derivatives, such as 1,3-dimethyluric acid and dimethylthiourea; allopurinol; thiols, such as glutathione and reduced glutathione and cysteine; trace elements, such as selenium, chromium, and boron; vitamins, including their precursors and derivatives, such as vitamin A, vitamin C (including its derivatives and salts such as sodium ascorbate and palmitoyl ascorbic acid) and vitamin E (and its derivatives and salts, such as alpha-, beta-, gamma-, delta-, epsilon-, zeta-, and eta-tocopherols, tocopherol acetate and alpha-tocotrienol); chromanol-alpha-C6; 6-hydroxy-2,5,7,8-tetramethylchroma-2 carboxylic acid (Trolox) and derivatives; extraneous proteins, such as gelatin and albumin; tris-3-methyl-1-phenyl-2-pyrazolin-5-one (MCI-186); citiolone; puercetin; chrysin; dimethyl sulfoxide (DMSO); piperazine diethanesulfonic acid (PIPES); imidazole; methoxypsoralen (DOPS); 1,2-dithiane-4,5-diol; reducing substances, such as butylated hydroxyanisole (BHA) and butylated hydroxytoluene (BHT); cholesterol, including derivatives and its various oxidized and reduced forms thereof, such as low density lipoprotein (LDL), high density lipoprotein (HDL), very low density lipoprotein (VLDL), etc.; probucol; indole derivatives; thimerosal; lazaroid and tirilazad mesylate; proanthenols; proanthocyanidins; ammonium sulfate; Pegorgotein (PEG-SOD); N-tert-butyl-alpha-phenylnitrone (PBN); 4-hydroxy-2,2,6,6-tetramethylpiperidin-1-oxyl (Tempol); mixtures of ascorbate, urate and Trolox C (Asc/urate/Trolox C); peptides, such as Gly—Gly and L-carnosine, in which each amino acid may be in its D and/or L form; reduced glutathione; diosmin; pupurogalin; gallic acid and its derivatives, including, but not limited to, propyl gallate, sodium formaldehyde sulfoxylate and silymarin; urea; tert-butylhydroquinone; circumin; capsaicin; coumarins; isothiocyanates; pycnogenal; allyl-cysteines; triterpenoids, genistein; cinnamaldehyde; and bergamottin. Particularly preferred examples include single stabilizers or combinations of stabilizers that are effective at quenching both Type I and Type II photodynamic reactions. Such single stabilizers or combinations of stabilizers are termed "combination stabilizer(s)" herein. Also particularly preferred are volatile stabilizers, which can be applied as a gas and/or easily removed by evaporation, low pressure and similar methods.

As used herein, the term "residual solvent content" is intended to mean the amount or proportion of freely available liquid in the preparation of one or more glycosidases. Freely available liquid means the liquid, such as water or an organic solvent (e.g., ethanol, isopropanol, polyethylene glycol, etc.), present in the preparation being sterilized that is not bound to or complexed with one or more of the non-liquid components of the preparation. Freely available liquid includes intracellular water. The residual solvent contents related as water referenced herein refer to levels determined by the FDA approved, modified Karl Fischer method (Meyer and Boyd, *Analytical Chem.*, 31:215–219, 1959; May, et al., *J. Biol. Standardization*, 10:249–259, 1982; Centers for Biologics Evaluation and Research, FDA, or by near infrared spectroscopy. Quantitation of the residual levels of other solvents may be determined by means well known in the art, depending upon which solvent is employed. The proportion of residual solvent to solute may also be considered to be a reflection of the concentration of the solute within the solvent. When so expressed, the greater the concentration of the solute, the lower the amount of residual solvent.

As used herein, the term "sensitizer" is intended to mean a substance that selectively targets viral, mold, fungal, bacterial, prion and/or parasitic contaminants or pathogens, rendering them more sensitive to inactivation by radiation, therefore permitting the use of a lower rate or dose of radiation and/or a shorter time of irradiation than in the absence of the sensitizer. Illustrative examples of suitable sensitizers include, but are not limited to, the following: psoralen and its derivatives and analogs (including 3-carboethoxy psoralens); inactines and their derivatives and analogs; angelicins, khellins and coumarins which contain a halogen substituent and a water solubilization moiety, such as quaternary ammonium ion or phosphonium ion; nucleic acid binding compounds; brominated hematoporphyrins; phthalocyanines; purpurins; porphyrins; halogenated or metal atom-substituted derivatives of dihematoporphyrin esters, hematoporphyrin derivatives, benzoporphyrin derivatives, hydrodibenzoporphyrin dimaleimide, hydrodibenzoporphyrin, dicyano disulfone, tetracarbethoxy hydrodibenzoporphyrin, and tetracarbethoxy hydrodibenzoporphyrin dipropionamide; doxorubicin and daunomycin, which may be modified with halogens and/or metal atoms; netropsin; BD peptide, S2 peptide; S-303 (ALE compound); dyes, such as hypericin, methylene blue, eosin, fluoresceins (and their derivatives), flavins, merocyanine 540; photoactive compounds, such as bergapten; and SE peptide.

As used herein, the term "radiation" is intended to mean radiation of sufficient energy to sterilize at least some component of the irradiated preparation of one or more glycosidases. Types of radiation include, but are not limited to, the following: (i) corpuscular (streams of subatomic particles such as neutrons, electrons, and/or protons); and (ii) electromagnetic (originating in a varying electromagnetic field, such as radio waves, visible (both mono and polychromatic) and invisible light, infrared, ultraviolet radiation, x-radiation, and gamma rays and mixtures thereof). Such radiation is often described as either ionizing (capable of producing ions in irradiated materials) radiation, such as gamma rays, and non-ionizing radiation, such as visible light. The sources of such radiation may vary and, in general, the selection of a specific source of radiation is not critical provided that sufficient radiation is given in an appropriate time and at an appropriate rate to effect sterilization. In practice, gamma radiation is usually produced by isotopes of Cobalt or Cesium, while X-rays are produced by machines that emit X-radiation, and electrons are often used to sterilize materials in a method known as "E-beam" irradiation that involves their production via a machine.

As used herein, the term "to protect" is intended to mean to reduce any damage to the preparation of one or more glycosidases being irradiated, that would otherwise result from the irradiation of that material, to a level that is insufficient to preclude the safe and effective use of the material following irradiation. In other words, a substance or process "protects" a preparation of one or more glycosidases from radiation if the presence of that substance or carrying out that process results in less damage to the material from irradiation than in the absence of that substance or process. Thus, a preparation of one or more glycosidases may be used safely and effectively after irradiation in the presence of a substance or following performance of a process that "protects" the material, but could not be used safely and effectively after irradiation under identical conditions but in the absence of that substance or the performance of that process.

B. Particularly Preferred Embodiments

A first preferred embodiment of the present invention is directed to a method for sterilizing a preparation of one or more glycosidases that is sensitive to radiation comprising irradiating the preparation of one or more glycosidases with radiation for a time effective to sterilize the material at a rate effective to sterilize the material and to protect the material from radiation.

Another preferred embodiment of the present invention is directed to a method for sterilizing a preparation of one or more glycosidases that is sensitive to radiation comprising: (i) adding to a preparation of one or more glycosidases at least one stabilizer in an amount effective to protect the preparation of one or more glycosidases from radiation; and (ii) irradiating the preparation of one or more glycosidases with radiation at an effective rate for a time effective to sterilize the material.

Another preferred embodiment of the present invention is directed to a method for sterilizing a preparation of one or more glycosidases that is sensitive to radiation comprising: (i) reducing the residual solvent content of a preparation of one or more glycosidases to a level effective to protect the preparation of one or more glycosidases from radiation; and (ii) irradiating the preparation of one or more glycosidases with radiation at an effective rate for a time effective to sterilize the preparation of one or more glycosidases.

Another preferred embodiment of the present invention is directed to a method for sterilizing a preparation of one or more glycosidases that is sensitive to radiation comprising: (i) reducing the temperature of a preparation of one or more glycosidases to a level effective to protect the preparation of one or more glycosidases from radiation; and (ii) irradiating the preparation of one or more glycosidases with radiation at an effective rate for a time effective to sterilize the preparation of one or more glycosidases.

Another preferred embodiment of the present invention is directed to a method for sterilizing a preparation of one or more glycosidases that is sensitive to radiation comprising: (i) applying to the preparation of one or more glycosidases a stabilizing process selected from the group consisting of: (a) reducing the residual solvent content of a preparation of one or more glycosidases, (b) adding to the preparation of one or more glycosidases at least one stabilizer, and (c) reducing the temperature of the preparation of one or more glycosidases; and (ii) irradiating the preparation of one or more glycosidases with radiation at an effective rate for a time effective to sterilize the preparation of one or more glycosidases, wherein the stabilizing process and the rate of irradiation are together effective to protect the preparation of one or more glycosidases from radiation.

Another preferred embodiment of the present invention is directed to a method for sterilizing a preparation of one or more glycosidases that is sensitive to radiation comprising: (i) applying to the preparation of one or more glycosidases at least two stabilizing processes selected from the group consisting of: (a) reducing the residual solvent content of a preparation of one or more glycosidases, (b) adding to the preparation of one or more glycosidases at least one stabilizer, and (c) reducing the temperature of the preparation of one or more glycosidases; and (ii) irradiating the preparation of one or more glycosidases with radiation at an effective rate for a time effective to sterilize the preparation of one or more glycosidases, wherein the stabilizing processes may be performed in any order and are together effective to protect the preparation of one or more glycosidases from radiation.

According to certain methods of the present invention, a stabilizer is added to the preparation of one or more glycosidases prior to irradiation of the preparation of one or more glycosidases with radiation. This stabilizer is added in an amount that is effective to protect the preparation of one or more glycosidases from the radiation. Suitable amounts of stabilizer may vary depending upon certain features of the particular method(s) of the present invention being employed, such as the nature and characteristics of the particular preparation of one or more glycosidases and/or stabilizer being used, and/or the intended use of the preparation of one or more glycosidases being irradiated, and can be determined empirically by one skilled in the art.

According to certain methods of the present invention, the residual solvent content of the preparation of one or more glycosidases is reduced prior to irradiation of the preparation of one or more glycosidases with radiation. The residual solvent content is reduced to a level that is effective to protect the preparation of one or more glycosidases from the radiation. Suitable levels of residual solvent content may vary depending upon certain features of the particular method(s) of the present invention being employed, such as the nature and characteristics of the particular preparation of one or more glycosidases and/or stabilizer being used, and/or the intended use of the preparation of one or more glycosidases being irradiated, and can be determined empirically by one skilled in the art. There may be preparations for which it is desirable to maintain the residual solvent content to within a particular range, rather than a specific value, for example when the solvent, or at least one of the solvents in a mixture, is also a stabilizer, such as an alcohol (e.g. ethanol) or dialkyl ketone (e.g. acetone).

When the preparation of one or more glycosidases is in a liquid or solid phase, more preferably when it is in a solid phase, and particularly preferably when the solvent is water, the residual solvent content is generally less than about 15%, typically less than about 10%, more typically less than about 9%, even more typically less than about 8%, usually less than about 5%, preferably less than about 3.0%, more preferably less than about 2.0%, even more preferably less than about 1.0%, still more preferably less than about 0.5%, still even more preferably less than about 0.2% and most preferably less than about 0.08%.

The solvent may preferably be a non-aqueous solvent, more preferably a non-aqueous solvent that is not prone to the formation of free-radicals upon irradiation, and most preferably a non-aqueous solvent that is not prone to the formation of free-radicals upon irradiation and that has little or no dissolved oxygen or other gas(es) that is (are) prone to the formation of free-radicals upon irradiation. Volatile non-aqueous solvents are particularly preferred, even more particularly preferred are non-aqueous solvents that are stabilizers, such as ethanol and acetone.

In certain embodiments of the present invention, the solvent may be a mixture of water and a non-aqueous solvent or solvents, such as ethanol and/or acetone. In such embodiments, the non-aqueous solvent(s) is preferably a non-aqueous solvent that is not prone to the formation of free-radicals upon irradiation, and most preferably a non-aqueous solvent that is not prone to the formation of free-radicals upon irradiation and that has little or no dissolved oxygen or other gas(es) that is (are) prone to the formation of free-radicals upon irradiation. Volatile non-aqueous solvents are particularly preferred, even more particularly preferred are non-aqueous solvents that are stabilizers, such as ethanol and acetone.

In a preferred embodiment, when the residual solvent is water, the residual solvent content of a biological material is reduced by dissolving or suspending the biological material in a non-aqueous solvent that is capable of dissolving water. Preferably, such a non-aqueous solvent is not prone to the formation of free-radicals upon irradiation and has little or no dissolved oxygen or other gas(es) that is (are) prone to the formation of free-radicals upon irradiation.

When the biological material is in a liquid phase, reducing the residual solvent content may be accomplished by any of a number of means, such as by increasing the solute concentration. In this manner, the concentration of the biological material dissolved within the solvent may be increased to generally at least about 0.5%, typically at least about 1%, usually at least about 5%, preferably at least about 10%, more preferably at least about 15%, even more preferably at least about 20%, still even more preferably at least about 25%, and most preferably at least about 50%.

In certain embodiments of the present invention, the residual solvent content of a particular biological material may be found to lie within a range, rather than at a specific point. Such a range for the preferred residual solvent content of a particular biological material may be determined empirically by one skilled in the art.

While not wishing to be bound by any theory of operability, it is believed that the reduction in residual solvent content reduces the degrees of freedom of the preparation of one or more glycosidases, reduces the number of targets for free radical generation and may restrict the solubility or diffusion of these free radicals. Similar results might therefore be achieved by lowering the temperature of the preparation of one or more glycosidases below its eutectic point or below its freezing point, or by vitrification to likewise reduce the degrees of freedom of the preparation of one or more glycosidases. These results may permit the use of a higher rate and/or dose of radiation than might otherwise be acceptable. Thus, the methods described herein may be carried out at any temperature that doesn't result in an unacceptable level of damage to the preparation. Preferably, the methods described herein are performed at ambient temperature or below ambient temperature, such as below the eutectic point or freezing point of the preparation of one or more glycosidases being irradiated.

In accordance with the methods of the present invention, an "acceptable level" of damage may vary depending upon certain features of the particular method(s) of the present invention being employed, such as the nature and characteristics of the particular preparation of one or more glycosidases and/or stabilizer being used, and/or the intended use of the preparation of one or more glycosidases being irradiated, and can be determined empirically by one skilled in the art. An "unacceptable level" of damage would therefore be a level of damage that would preclude the safe and effective use of the preparation of one or more glycosidases being sterilized. The particular level of damage in a given preparation of one or more glycosidases may be determined using any of the methods and techniques known to one skilled in the art.

The residual solvent content of a preparation of one or more glycosidases may be reduced by any of the methods and techniques known to those skilled in the art for reducing solvent from a preparation of one or more glycosidases without producing an unacceptable level of damage to the preparation. Such methods include, but are not limited to, evaporation, concentration, centrifugal concentration, vitrification, addition of solute, lyophilization (with or without the prior addition of ascorbate) and spray-drying.

A particularly preferred method for reducing the residual solvent content of a preparation of one or more glycosidases is lyophilization, even more preferred is lyophilization following the addition of ascorbate.

Another particularly preferred method for reducing the residual solvent content of a preparation of one or more glycosidases is vitrification, which may be accomplished by any of the methods and techniques known to those skilled in the art, including the addition of solute and or additional solutes, such as sucrose, to raise the eutectic point of the biological material, followed by a gradual application of reduced pressure to the biological material in order to remove the residual solvent, such as water. The resulting glassy material will then have a reduced residual solvent content.

According to certain methods of the present invention, the preparation of one or more glycosidases to be sterilized may be immobilized upon a solid surface by any means known and available to one skilled in the art. For example, the preparation of one or more glycosidases to be sterilized may be present as a coating or surface on a biological or non-biological substrate.

The radiation employed in the methods of the present invention may be any radiation effective for the inactivation of one or more biological contaminants or pathogens of the preparation of one or more glycosidases being treated. The radiation may be corpuscular, including E-beam radiation. Preferably the radiation is electromagnetic radiation, including visible light, infrared, x-radiation, UV light and mixtures of various wavelengths of electromagnetic radiation. A particularly preferred form of radiation is gamma radiation.

According to the methods of the present invention, the preparation of one or more glycosidases to be sterilized is irradiated with the radiation at a rate effective for the inactivation of one or more biological contaminants or pathogens of the preparation. Suitable rates of irradiation may vary depending upon certain features of the methods of the present invention being employed, such as the nature and characteristics of the particular preparation of one or more glycosidases being irradiated, the particular form of radiation involved and/or the particular biological contaminants or pathogens being inactivated. Suitable rates of irradiation can be determined empirically by one skilled in the art. Preferably, the rate of irradiation is constant for the duration of the sterilization procedure. When this is impractical or otherwise not desired, a variable or discontinuous irradiation may be utilized.

According to the methods of the present invention, the rate of irradiation may be optimized to produce the most advantageous combination of product recovery and time required to complete the operation. Both low ($\leq 3$ kGy/hour) and high (>3 kGy/hour) rates may be utilized in the methods described herein to achieve such results.

According to a particularly preferred embodiment of the present invention, the rate of irradiation is not more than about 3.0 kGy/hour, more preferably between about 0.1 kGy/hr. and 3.0 kGy/hr, even more preferably between about 0.25 kGy/hr and 2.0 kGy/hour, still even more preferably between about 0.5 kGy/hr and 1.5 kGy/hr and most preferably between about 0.5 kGy/hr and 1.0 kGy/hr.

According to another particularly preferred embodiment of the present invention, the rate of irradiation is at least about 3.0 kGy/hr., more preferably at least about 6 kGy/hr., even more preferably at least about 16 kGy/hr., and even more preferably at least about 30 kGy/hr and most preferably at least about 45 kGy/hr or greater.

According to another particularly preferred embodiment of the present invention, the maximum acceptable rate of irradiation is inversely proportional to the molecular mass of the biological material being irradiated.

According to the methods of the present invention, the preparation of one or more glycosidases to be sterilized is irradiated with the radiation for a time effective for the inactivation of one or more biological contaminants or pathogens of the preparation of one or more glycosidases. Combined with irradiation rate, the appropriate irradiation time results in the appropriate dose of irradiation being applied to the preparation of one or more glycosidases. Suitable irradiation times may vary depending upon the particular form and rate of radiation involved, the nature and characteristics of the particular preparation of one or more glycosidases being irradiated and/or the particular biological contaminants or pathogens being inactivated. Suitable irradiation times can be determined empirically by one skilled in the art.

According to the methods of the present invention, the preparation of one or more glycosidases to be sterilized is irradiated with radiation up to a total dose effective for the inactivation of one or more active biological contaminants or pathogens in the material, while not producing an unacceptable level of damage to that material. Suitable total doses of radiation may vary depending upon certain features of the methods of the present invention being employed, such as the nature and characteristics of the particular preparation being irradiated, the particular form of radiation involved and/or the particular active biological contaminant or pathogen being inactivated. Suitable total doses of radiation can be determined empirically by one skilled in the art. Preferably, the total dose of radiation is at least 25 kGy, more preferably at least 45 kGy, even more preferably at least 75 kGy, and still more preferably at least 100 kGy or greater, such as 150 kGy or 200 kGy or greater.

The particular geometry of the preparation of one or more glycosidases being irradiated, such as the thickness and distance from the source of radiation, may be determined empirically by one skilled in the art. A preferred embodiment is a geometry that provides for an even rate of irradiation throughout the preparation. A particularly preferred embodiment is a geometry that results in a short path length for the radiation through the preparation, thus minimizing the differences in radiation dose between the front and back of the preparation. This may be further minimized in some preferred geometries, particularly those wherein the preparation has a constant radius about its axis that is perpendicular to the radiation source, by the utilization of a means of rotating the preparation about said axis.

Similarly, according to certain methods of the present invention, an effective package for containing the preparation during irradiation is one which combines stability under the influence of irradiation, and which minimizes the interactions between the package and the radiation. Preferred packages maintain a seal against the external environment before, during and post-irradiation, and are not reactive with the preparation within, nor do they produce chemicals that may interact with the preparation within. Particularly preferred examples include but are not limited to containers that comprise glasses stable when irradiated, stoppered with stoppers made of rubber that is relatively stable during radiation and liberates a minimal amount of compounds from within, and sealed with metal crimp seals of aluminum or other suitable materials with relatively low Z numbers. Suitable materials can be determined by measuring their physical performance, and the amount and type of reactive leachable compounds post-irradiation and by examining other characteristics known to be important to the containment of biological materials empirically by one skilled in the art.

According to certain methods of the present invention, an effective amount of at least one sensitizing compound may optionally be added to the preparation of one or more glycosidases prior to irradiation, for example to enhance the effect of the irradiation on the biological contaminant(s) or pathogen(s) therein, while employing the methods described herein to minimize the deleterious effects of irradiation upon the preparation of one or more glycosidases. Suitable sensitizers are known to those skilled in the art, and include, for example, psoralens and their derivatives and analogs and inactines and their derivatives and analogs.

According to the methods of the present invention, the irradiation of the preparation of one or more glycosidases may occur at any temperature that is not deleterious to the preparation of one or more glycosidases being sterilized. According to one preferred embodiment, the preparation of one or more glycosidases is irradiated at ambient temperature. According to an alternate preferred embodiment, the preparation of one or more glycosidases is irradiated at reduced temperature, i.e. a temperature below ambient temperature, such as 0° C., −20° C., −40° C., −60° C., −78° C. or −196° C. According to this embodiment of the present invention, the preparation of one or more glycosidases is preferably irradiated at or below the freezing or eutectic point of the preparation of one or more glycosidases. According to another alternate preferred embodiment, the preparation of one or more glycosidases is irradiated at elevated temperature, i.e. a temperature above ambient temperature, such as 37° C., 60° C., 72° C. or 80° C. While not wishing to be bound by any theory, the use of elevated temperature may enhance the effect of irradiation on the biological contaminant(s) or pathogen(s) and therefore allow the use of a lower total dose of radiation.

Most preferably, the irradiation of the preparation of one or more glycosidases occurs at a temperature that protects the preparation from radiation. Suitable temperatures can be determined empirically by one skilled in the art.

In certain embodiments of the present invention, the temperature at which irradiation is performed may be found to lie within a range, rather than at a specific point. Such a range for the preferred temperature for the irradiation of a particular preparation of one or more glycosidases may be determined empirically by one skilled in the art.

According to the methods of the present invention, the irradiation of the preparation of one or more glycosidases may occur at any pressure which is not deleterious to the biological material being sterilized. According to one preferred embodiment, the preparation of one or more glycosidases is irradiated at elevated pressure. More preferably, the preparation of one or more glycosidases is irradiated at elevated pressure due to the application of sound waves, the use of a volatile, compression or other means known to those skilled in the art. While not wishing to be bound by any theory, the use of elevated pressure may enhance the effect of irradiation on the biological contaminant(s) or pathogen(s) and/or enhance the protection afforded by one or more stabilizers, and therefore allow the use of a lower total dose of radiation. Suitable pressures can be determined empirically by one skilled in the art.

Generally, according to the methods of the present invention, the pH of the preparation of one or more glycosidases undergoing sterilization is about 7. In some embodiments of the present invention, however, the preparation of one or more glycosidases may have a pH of less than 7, preferably less than or equal to 6, more preferably less than or equal to 5, even more preferably less than or equal to 4, and most preferably less than or equal to 3. In alternative embodiments of the present invention, the preparation of one or more glycosidases may have a pH of greater than 7, preferably greater than or equal to 8, more preferably greater than or equal to 9, even more preferably greater than or equal to 10, and most preferably greater than or equal to 11. According to certain embodiments of the present invention, the pH of the preparation undergoing sterilization is at or near the isoelectric point of the enzyme(s) contained in the preparation. According to other embodiments of the present invention, the pH of the preparation undergoing sterilization is at or near the pH at which at least one enzyme in the preparation has maximal affinity for its substrate(s). Suitable pH levels can be determined empirically by one skilled in the art.

Similarly, according to the methods of the present invention, the irradiation of the preparation of one or more glycosidases may occur under any atmosphere that is not deleterious to the preparation of one or more glycosidases being treated. According to one preferred embodiment, the preparation of one or more glycosidases is held in a low oxygen atmosphere or an inert atmosphere. When an inert atmosphere is employed, the atmosphere is preferably composed of a noble gas, such as helium or argon, more preferably a higher molecular weight noble gas, and most preferably argon. According to another preferred embodiment, the preparation of one or more glycosidases is held under vacuum while being irradiated. According to a particularly preferred embodiment of the present invention, a preparation of one or more glycosidases (lyophilized, liquid or frozen) is stored under vacuum or an inert atmosphere (preferably a noble gas, such as helium or argon, more preferably a higher molecular weight noble gas, and most preferably argon) prior to irradiation. According to an alternative preferred embodiment of the present invention, a liquid preparation of one or more glycosidases is held under low pressure, to decrease the amount of gas, particularly oxygen, dissolved in the liquid, prior to irradiation, either with or without a prior step of solvent reduction, such as lyophilization. Such degassing may be performed using any of the methods known to one skilled in the art.

In another preferred embodiment, where the preparation of one or more glycosidases contains oxygen or other gases dissolved within or associated with it, the amount of these gases within or associated with the preparation may be reduced by any of the methods and techniques known and available to those skilled in the art, such as the controlled reduction of pressure within a container (rigid or flexible) holding the preparation to be treated or by placing the preparation in a container of approximately equal volume.

It will be appreciated that the combination of one or more of the features described herein may be employed to further minimize undesirable effects upon the preparation of one or more glycosidases caused by irradiation, while maintaining adequate effectiveness of the irradiation process on the biological contaminant(s) or pathogen(s). For example, in addition to the use of a stabilizer, a particular preparation of one or more glycosidases may also be lyophilized, held at reduced temperature and kept under vacuum prior to irradiation to further minimize undesirable effects.

The sensitivity of a particular biological contaminant or pathogen to radiation is commonly calculated by determining the dose necessary to inactivate or kill all but 37% of the agent in a sample, which is known as the $D_{37}$ value. The desirable components of a preparation of one or more glycosidases may also be considered to have a $D_{37}$ value equal to the dose of radiation required to eliminate all but 37% of their desirable biological and physiological characteristics.

In accordance with certain preferred methods of the present invention, the sterilization of a preparation of one or more glycosidases is conducted under conditions that result in a decrease in the $D_{37}$ value of the biological contaminant or pathogen without a concomitant decrease in the $D_{37}$ value of the preparation of one or more glycosidases. In accordance with other preferred methods of the present invention, the sterilization of a preparation of one or more glycosidases is conducted under conditions that result in an increase in the $D_{37}$ value of the preparation of one or more glycosidases. In accordance with the most preferred methods of the present invention, the sterilization of a preparation of one or more glycosidases is conducted under conditions that result in a decrease in the $D_{37}$ value of the biological contaminant or pathogen and a concomitant increase in the $D_{37}$ value of the preparation of one or more glycosidases.

EXAMPLES

The following examples are illustrative, but not limiting, of the present invention. Other suitable modifications and adaptations are of the variety normally encountered by those skilled in the art, and are fully within the spirit and scope of the present invention. Unless otherwise noted, all gamma irradiation was accomplished using a $^{60}$Co source.

Example 1

In this experiment, the protective effect of ascorbate (200 mM) and a combination of ascorbate (200 mM) and Gly—Gly (200 mM) on a frozen galactosidase preparation was evaluated.

Method

In glass vials, 300 µl total volume containing 300 µg of enzyme (1 mg/ml) were prepared with either no stabilizer or the stabilizer of interest. Samples were irradiated with gamma radiation (45 kGy total dose, dose rate and temperature of 1.616 kGy/hr and −21.5° C. or 5.35 kGy/hr and −21.9° C.) and then assayed for structural integrity.

Structural integrity was determined by SDS-PAGE. Three 12.5% gels were prepared according to the following recipe: 4.2 ml acrylamide; 2.5 ml 4x-Tris (pH 8.8); 3.3 ml water; 100 µl 10% APS solution; and 10 µl TEMED (tetramethylethylenediamine). This solution was then placed in an electrophoresis unit with 1×Running Buffer (15.1 g Tris base; 72.0 g glycine; 5.0 g SDS in 1 l water, diluted 5-fold). Irradiated and control samples (1 mg/ml) were diluted with Sample Buffer (+/−beta-mercaptoethanol) in Eppindorf tubes and then centrifuged for several minutes. 20 µl of each diluted sample (~10 µg) were assayed.

Results

Figure 1B:
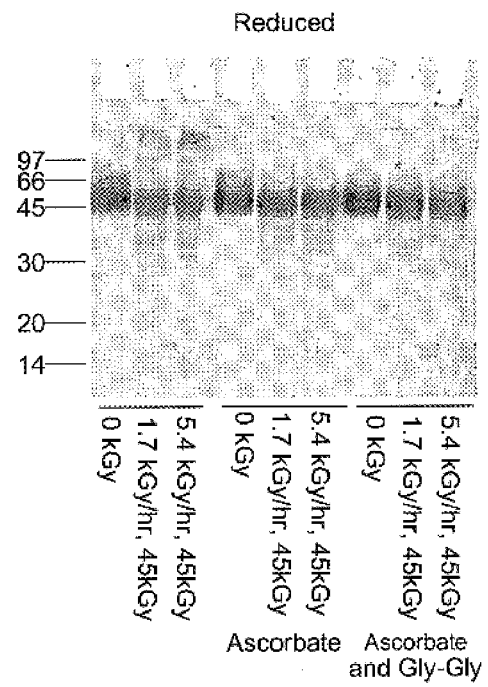

Liquid enzyme samples irradiated to 45 kGy in the abseloss of material and evidence of both aggregation and fragmentation. Much greater recovery of material was obtained from the irradiated samples containing ascorbate or a combination of ascorbate and Gly—Gly. The results of this experiment are shown in FIG. 1.

Example 2

In this experiment, the protective effect of ascorbate (200 mM) and a combination of ascorbate (200 mM) and Gly—Gly (200 mM) on a frozen galactosidase preparation was evaluated.

Method

Samples were prepared in 2 ml glass vials, each containing 52.6 µl of a glycosidase solution (5.7 mg/ml), and either no stabilizer or a stabilizer of interest, and sufficient water to make a total sample volume of 300 µl. Samples were irradiated with gamma radiation (45 kGy total dose, dose rate and temperature of either 1.616 kGy/hr and −21.5° C. or 5.35 kGy/hr and _21.9° C.) and then assayed for structural integrity.

Structural integrity was determined by reverse phase chromatography. 10 µl of sample were diluted with 90 µl solvent A and then injected onto an Aquapore RP-300 (c-8) column (2.1×30 mm) mounted in an Applied Biosystems 130A Separation System Microbore HPLC. Solvent A: 0.1% trifluoroacetic acid; solvent B: 70% acetonitrile, 30% water, 0.085% trifluoroacetic acid.

Results

Figure 2:
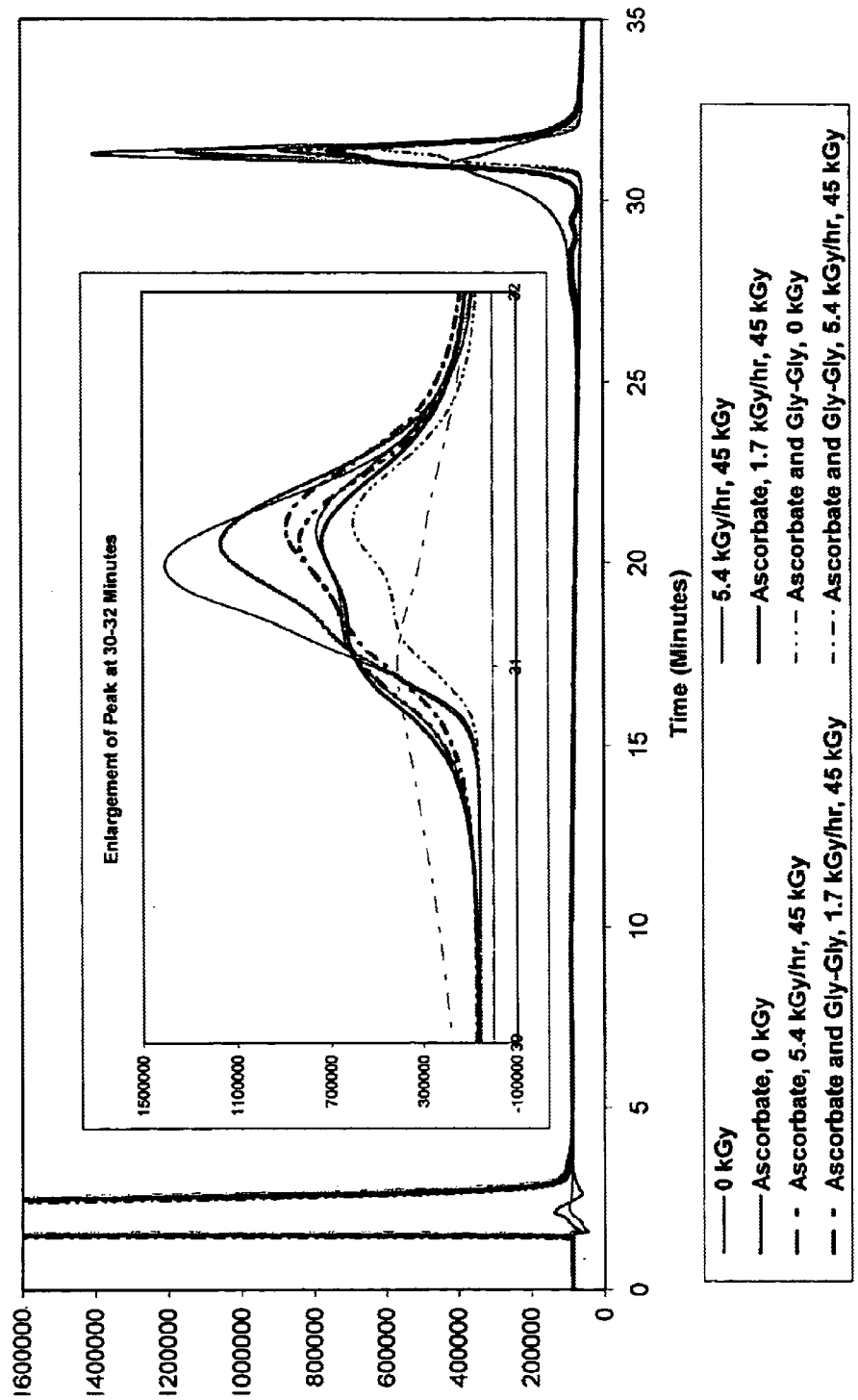
FIG. 2 is a graph showing the protective effect of stabilizers on a frozen glycosidase preparation.

Enzyme samples irradiated to 45 kGy in the absence of a stabilizer showed broadened and reduced peaks. Much greater recovery of material, as evidenced by significantly less reduction in peak size compared to control (FIG. 2), was obtained from the irradiated samples containing ascorbate or a combination of ascorbate and Gly—Gly.

Example 3

In this experiment, lyophilized galactosidase preparations were irradiated in the absence or presence of a stabilizer (100 mM sodium ascorbate).

Method

Glass vials containing 1 mg of enzyme were prepared with either no stabilizer or 100 mM sodium ascorbate (50 µl of 2M solution) and sufficient water to make 1 ml of sample. Samples were lyophilized, resulting in the following moisture levels: galactosidase with stabilizer, 3.4%; galactosidase without stabilizer, 3.2%. Lyophilized samples were irradiated with gamma radiation (45 kGy total dose at 1.8 kGy/hr and 4° C.) and then assayed for structural integrity.

Structural integrity was determined by SDS-PAGE. In an electrophoresis unit, 6 µg/lane of each sample was run at 120V on a 7.5%–15% acrylamide gradient gel with a 4.5% acrylamide stacker under non-reducing conditions.

Results

Lyophilized galactosidase samples irradiated to 45 kGy in the absence of a stabilizer showed significant recovery of intact enzyme with only some fragmentation. This contrasts to the much higher levels of degradation seen in the frozen liquid preparation described in Example 1, indicating that the reduction of solvent (water) significantly reduced radiation induced damage. Fragmentation was even further reduced by the addition of a stabilizer.

Figure 3:
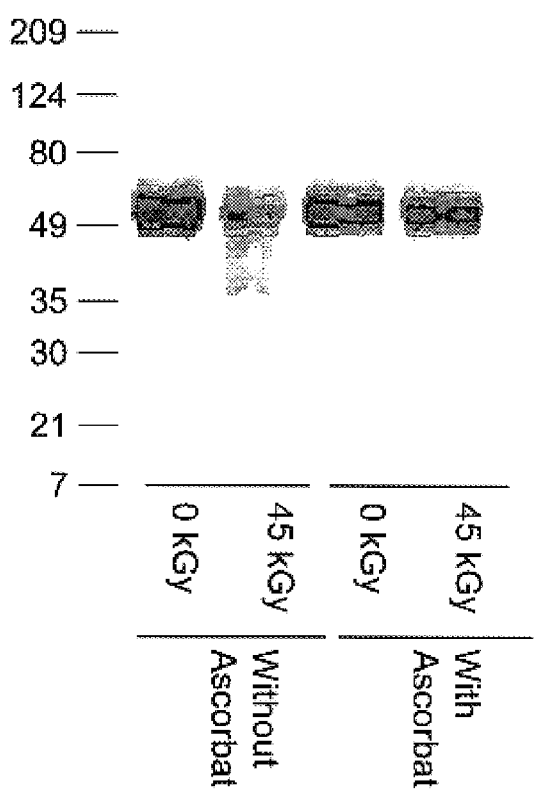
FIG. 3 shows the protective effect of ascorbate on a lyophilized glycosidase preparation.

The results of this experiment are shown in FIG. 3.

Example 4

In this experiment, lyophilized galactosidase preparations irradiated in the absence or presence of a stabilizer (200 mM sodium ascorbate or a combination of 200 mM ascorbate and 200 mM glycylglycine).

Methods

Samples were prepared in glass vials, each containing 300 µg of a lyophilized glycosidase and either no stabilizer or a stabilizer of interest. Samples were irradiated with gamma radiation to various total doses (10 kGy, 30 kGy and 50 kGy total dose, at a rate of 0.6 kGy/hr. at a temperature of −60° C.) and then assayed for structural integrity using SDS-PAGE.

Samples were reconstituted with water to a concentration of 1 mg/ml, diluted 1:1 with 2×sample buffer (15.0 ml 4×Upper Tris-SDS buffer (pH 6.8); 1.2 g sodium dodecyl sulfate;6 ml glycerol; sufficient water to make up 30 ml; either with or without 0.46 g dithiothreitol), and then heated at 80° C. for 10 minutes. 10 µl of each sample (containing 5 µg of enzyme) were loaded into each lane of a 10% polyacrylamide gel and run on an electrophoresis unit at 125V for about 1.5 hours.

Results

Figure 4A:
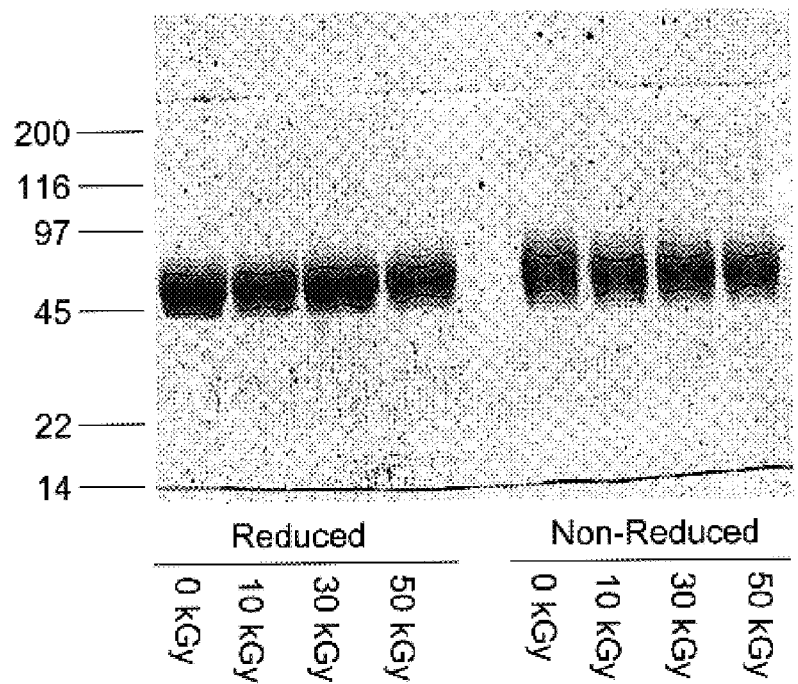
FIGS. 4A–4C are gels showing the protective effect of ascorbate (200 mM) and a combination of ascorbate (200 mM) and Gly—Gly (200 mM) on a lyophilized glycosidase preparation.
Figure 4B:
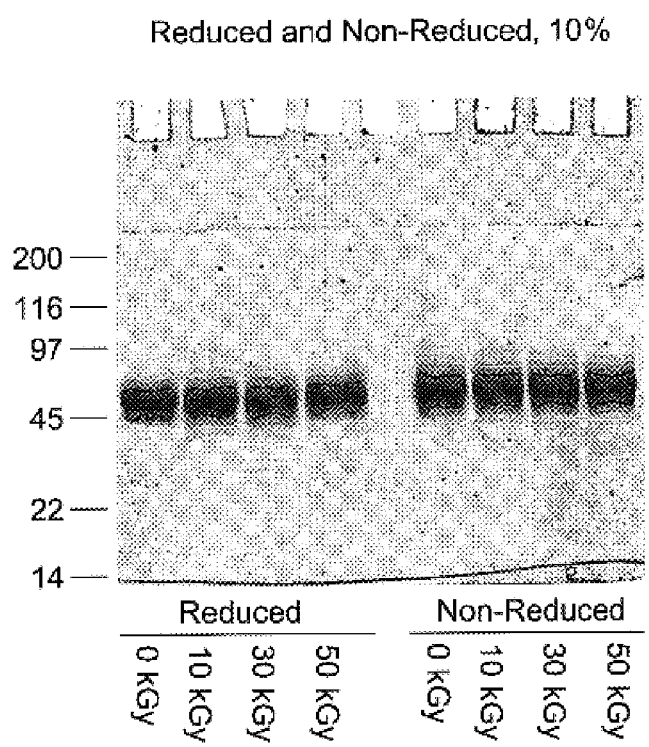
Figure 4C:
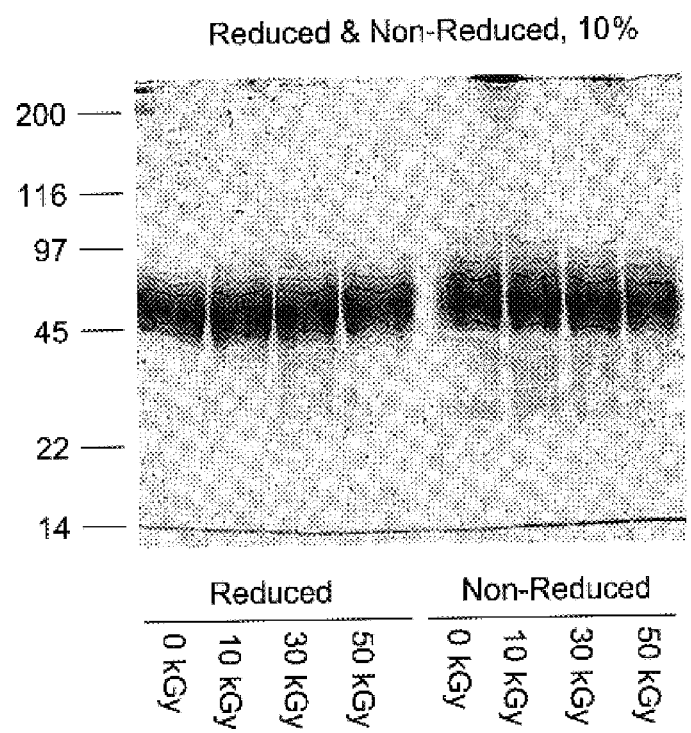

About 80% of the enzyme was recovered following irradiation of the samples containing no stabilizer. These samples had a visible precipitate post-irradiation, while those with a stabilizer did not. Thus the samples without stabilizer were actually more damaged than suggested by the gels in FIGS. 4A–4C, as the aggregated material could not be applied to the gels. Nevertheless, some degradation of the remaining soluble material without stabilizer was seen, particularly the emergence of a new band at approximately 116 kDa. Less degradation was observed in the samples containing ascorbate alone as the stabilizer, and even less degradation in the samples containing a combination of ascorbate and glycylglycine as the stabilizer. These results were better than those observed in the previous Example in which the preparation was lyophylized to reduce solvent (water) and irradiated at 4° C. indicating that the reduction in temperature to −60° C., along with increased concentrations of ascorbate and the addition of glycylglycine further reduced the damage to the glycosidase preparation.

Having now fully described this invention, it will be understood to those of ordinary skill in the art that the methods of the present invention can be carried out with a wide and equivalent range of conditions, formulations, and other parameters without departing from the scope of the invention or any embodiments thereof.

All patents and publications cited herein are hereby fully incorporated by reference in their entirety. The citation of any publication is for its disclosure prior to the filing date and should not be construed as an admission that such publication is prior art or that the present invention is not entitled to antedate such publication by virtue of prior invention.

The foregoing embodiments and advantages are merely exemplary and are not to be construed as limiting the present invention. The present teaching can be readily applied to other types of apparatuses. The description of the present invention is intended to be illustrative, and not to limit the scope of the claims. Many alternatives, modifications, and variations will be apparent to those skilled in the art.

What is claimed is:

1. A method for sterilizing a preparation of one or more glycosidases that is sensitive to radiation, said method comprising reducing the temperature of said preparation of one or more glycosidases to a temperature below ambient temperature, and irradiating said preparation of one or more glycosidases with radiation for a time effective to sterilize said preparation of one or more glycosidases at a rate effective to sterilize said preparation of one or more glycosidases and to protect said preparation of one or more glycosidases from said radiation.

2. The method according to claim 1, said method further comprising adding to said preparation of one or more glycosidases at least one stabilizer in an amount effective to protect said preparation of one or more glycosidases from said radiation prior to said irradiating.

3. The method according to claim 1, said method further comprising reducing the residual solvent content of said preparation of one or more glycosidases to a level effective to protect said preparation of one or more glycosidases from said radiation prior to said irradiating.

4. The method according to claim 1, said method further comprising applying to said preparation of one or more glycosidases prior to irradiating at least one stabilizing process selected from the group consisting of:
   (a) reducing the residual solvent content of said preparation of one or more glycosidases, and
      adding an effective amount of at least one stabilizer to said preparation of one or more glycosidases.

5. The method according to claim 1, said method further comprising applying to said preparation of one or more glycosidases prior to irradiating at least one stabilizing process selected from the group consisting of:

(a) reducing the residual solvent content of said preparation of one or more glycosidases, and adding an effective amount of at least one stabilizer to said preparation of one or more glycosidases, wherein said stabilizing processes are together effective to protect said preparation of one or more glycosidases from said radiation and further wherein said stabilizing processes may be performed in any order.

6. The method according to claim 3, 4 or 5, wherein said solvent is water.

7. The method according to claim 6, wherein said residual water content is reduced by the addition of an organic solvent.

8. The method according to claim 3, 4 or 5, wherein said solvent is an organic solvent.

9. The method according to claim 3, 4 or 5 wherein said prepartion of one or more glycosidases is suspended in an organic solvent following reduction of said residual solvent content.

10. The method according to claim 1, wherein said effective rate is not more than 3.0 kGy/hour.

11. The method according to claim 1, wherein said effective rate is not more than 2.0 kGy/hour.

12. The method according to claim 1, wherein said effective rate is not more than 1.0 kGy/hour.

13. The method according to claim 1, wherein said effective rate is not more than 0.3 kGy/hour.

14. The method according to claim 1, wherein said effective rate is not more than 3.0 kGy/hour.

15. The method according to claim 1, wherein said effective rate is not more than 6.0 kGy/hour.

16. The method according to claim 1, wherein said effective rate is not more than 18.0 kGy/hour.

17. The method according to claim 1, wherein said effective rate is not more than 30.0 kGy/hour.

18. The method according to claim 1, wherein said effective rate is not more than 45 kGy/hour.

19. The method according to claim 1, wherein said preparation of one or more glycosidases is maintained in a low oxygen atmosphere.

20. The method according to claim 1, wherein said preparation of one or more glycosidases is maintained in an atmosphere comprising at least one noble gas.

21. The method according to claim 20, wherein said noble gas is argon.

22. The method according to claim 1, wherein said preparation of one or more glycosidases is maintained in a vacuum.

23. The method according to claim 3, 4 or 5, wherein said residual solvent content is reduced by a method selected from the group consisting of lyophilization, drying, concentration, addition of solute, evaporation, chemical extraction, spray-drying, vitrification and combinations of two or more thereof.

24. The method according to claim 3, 4 or 5, wherein said residual solvent content is less than 15%.

25. The method according to claim 3, 4 or 5, wherein said residual solvent content is less than 10%.

26. The method according to claim 3, 4 or 5, wherein said residual solvent content is less than 3%.

27. The method according to claim 3, 4 or 5 wherein said residual solvent content is less than 2%.

28. The method according to claim 3, 4 or 5 wherein said residual solvent content is less than 1%.

29. The method according to claim 3, 4 or 5, wherein said residual solvent content is less than 0.5%.

30. The method according to claim 3, 4 or 5, wherein said residual solvent content is less than 0.08%.

31. The method according to claim 1, wherein at least one sensitizer is added to said preparation of one or more glycosidases prior to said step of irradiating said preparation of one or more glycosidases.

32. The method according to claim 1, wherein said preparation of one or more glycosidases contains at least one biological contaminant or pathogen selected from the group consisting of viruses, bacteria, yeasts, molds, fungi, parasites, and prions or similar agents responsible, alone or in combination, for TSEs.

33. The method according to claim 2, 4 or 5, wherein said at least one stabilizer is an antioxidant.

34. The method according to claim 2, 4 or 5 wherein said at least one stabilizer comprises a free radical scavenger.

35. The method according to claim 2, 4 or 5 wherein said at least one stabilizer is a combination stabilizer.

36. The method according to claim 2, 4 or 5, wherein said at least one stabilizer comprises a ligand.

37. The method according to claim 36, wherein said ligand is heparin.

38. The method according to claim 36, wherein said ligand is a substrate or substrate analog of at least one glycosidase contained in said preparation of one or more glycosidases.

39. The method according to claim 2, 4 or 5, wherein said at least one stabilizer reduces damage due to reactive oxygen species.

40. The method according to claim 2, 4 or 5 wherein said at least one stabilizer is selected from the group consisting of: ascorbic acid or a salt or ester thereof; glutathione; 6-hydroxy-2,5,7,8-tetramethylchroman-2-carboxylic acid; uric acid or a salt or ester thereof; methionine; histidine; N-acetyl cysteine; lipoic acid; sodium formaldehyde sulfoxylate; gallic acid or a derivative thereof; propyl gallate and mixtures of two or more thereof.

41. The method according to claim 40, wherein said mixtures of two or more additional stabilizers are selected from the group consisting of: mixtures of ascorbic acid, or a salt or ester thereof, and uric acid, or a salt or ester thereof; mixtures of ascorbic acid, or a salt or ester thereof, and 6-hydroxy-2,5,7,8-tetramethylchroman-2-carboxylic acid; mixtures of ascorbic acid, or a salt or ester thereof, uric acid, or a salt or ester thereof; and 6-hydroxy-2,5,7,8-tetramethylchroman-2-carboxylic acid; and mixtures of uric acid, or a salt or ester thereof, lipoic acid, sodium formaldehyde sulfoxylate, gallic acid or a derivative thereof, propyl gallate and 6-hydroxy-2,5,7,8-tetramethylchroman-2-carboxylic acid.

42. The method according to claim 2, 4 or 5, wherein said at least one stabilizer is comprises a dipeptide stabilizer.

43. The method according to claim 42, wherein said dipeptide stabilizer is selected from the group consisting of glycyl-glycine (Gly—Gly), carnosine, anserine and combinations of two or more thereof.

44. The method according to claim 1, wherein said radiation is corpuscular radiation or electromagnetic radiation, or a mixture thereof.

45. The method according to claim 44, wherein said electromagnetic radiation is selected from the group consisting of radio waves, microwaves, visible and invisible light, ultraviolet light, x-ray radiation, gamma radiation and combinations thereof.

46. The method according to claim 1, wherein said radiation is gamma radiation.

47. The method according to claim 1, wherein said radiation is E-beam radiation.

48. The method according to claim 1, wherein said radiation is visible light.

49. The method according to claim 1, wherein said radiation is ultraviolet light.

50. The method according to claim 1, wherein said radiation is x-ray radiation.

51. The method according to claim 1, wherein said radiation is polychromatic visible light.

52. The method according to claim 1, wherein said radiation is infrared.

53. The method according to claim 1, wherein said radiation is a combination of one or more wavelengths of visible and ultraviolet light.

54. The method according to claim 1, wherein said radiation is conducted at a temperature below ambient temperature.

55. The method according to claim 1, wherein said radiation is conducted below the freezing point of said preparation of one or more glycosidases.

56. The method according to claim 1, wherein said irradiation is conducted below the eutectic point of said preparation of one or more glycosidases.

* * * * *